United States Patent
Clark et al.

(10) Patent No.: US 12,121,664 B2
(45) Date of Patent: Oct. 22, 2024

(54) CONDUITS AND OTHER COMPONENTS WITH WICKING PROPERTIES AND ASSOCIATED METHODS

(71) Applicant: Fisher & Paykel Healthcare Limited, Auckland (NZ)

(72) Inventors: Andrew Derek Clark, Auckland (NZ); Thomas James Edwards, Auckland (NZ); Hayley-Ann Adamson, Auckland (NZ); Leo Mckenzie Rodger, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 815 days.

(21) Appl. No.: 17/047,845

(22) PCT Filed: Apr. 18, 2019

(86) PCT No.: PCT/NZ2019/050040
§ 371 (c)(1),
(2) Date: Oct. 15, 2020

(87) PCT Pub. No.: WO2019/203664
PCT Pub. Date: Oct. 24, 2019

(65) Prior Publication Data
US 2021/0138173 A1    May 13, 2021

Related U.S. Application Data

(60) Provisional application No. 62/659,457, filed on Apr. 18, 2018.

(51) Int. Cl.
*A61M 16/08* (2006.01)
*A61M 16/00* (2006.01)
(Continued)

(52) U.S. Cl.
CPC .... *A61M 16/0808* (2013.01); *A61M 16/0003* (2014.02); *A61M 16/0875* (2013.01);
(Continued)

(58) Field of Classification Search
CPC .......... A61M 16/0808; A61M 16/0875; A61M 16/0883; A61M 16/1095; A61M 16/16
See application file for complete search history.

(56) References Cited

U.S. PATENT DOCUMENTS 4,391,271 A * 7/1983 Blanco .............. A61M 16/0833
128/205.12
9,327,093 B2    5/2016 Klasek et al.
(Continued)

FOREIGN PATENT DOCUMENTS

EP        2830695        12/2017
WO    WO 2011/077250    6/2011
(Continued)

OTHER PUBLICATIONS

International Search Report, PCT/NZ2019/050040, dated Aug. 8, 2019, 12 pages.
(Continued)

*Primary Examiner* — Margaret M Luarca
(74) *Attorney, Agent, or Firm* — Knobbe Martens Olson & Bear, LLP

(57) ABSTRACT

In one embodiment, a medical circuit component for use with humidified gases is described. The medical circuit conduit includes: a body comprising a wall having an inner surface that defines a space within which humidified gases may flow and/or be contained; and moisture transport means and/or element(s) at least partially coupled to and/or at least partially integrated into at least a part of the wall, the moisture transport means and/or element(s) being configured to receive moisture from vapors and/or liquid inside the
(Continued)

space and transport at least some of said moisture away from where it was received.

14 Claims, 7 Drawing Sheets

(51) Int. Cl.
*A61M 16/10* (2006.01)
*A61M 16/16* (2006.01)
(52) U.S. Cl.
CPC .... *A61M 16/0883* (2014.02); *A61M 16/1095* (2014.02); *A61M 16/16* (2013.01); *A61M 2205/3368* (2013.01); *A61M 2207/00* (2013.01)

(56) References Cited

U.S. PATENT DOCUMENTS

| 10,773,043 | B2 | 9/2020 | Dwyer et al. |
| 2001/0054422 | A1 | 12/2001 | Smith et al. |
| 2002/0002976 | A1 | 1/2002 | Smith et al. |
| 2004/0099268 | A1 | 5/2004 | Smith et al. |
| 2004/0118401 | A1 | 6/2004 | Smith et al. |
| 2012/0174924 | A1 | 7/2012 | Smith et al. |
| 2013/0081620 | A1 | 4/2013 | Korneff et al. |
| 2013/0255672 | A1 | 10/2013 | Varga et al. |
| 2016/0015926 | A1 | 1/2016 | Hermez et al. |
| 2016/0101258 | A1 | 4/2016 | Rustad et al. |
| 2016/0303342 | A1* | 10/2016 | Dwyer .............. A61M 16/0875 |
| 2017/0000967 | A1 | 1/2017 | Sims et al. |

FOREIGN PATENT DOCUMENTS

| WO | WO 2012/033421 | 3/2012 |
| WO | WO 2014/003579 | 1/2014 |
| WO | WO 2014/142677 | 9/2014 |
| WO | WO 2016/036260 | 3/2016 |

OTHER PUBLICATIONS

International Preliminary Report on Patentability for International Application No. PCT/NZ2019/050040 dated Oct. 20, 2020; 12 pages.

* cited by examiner

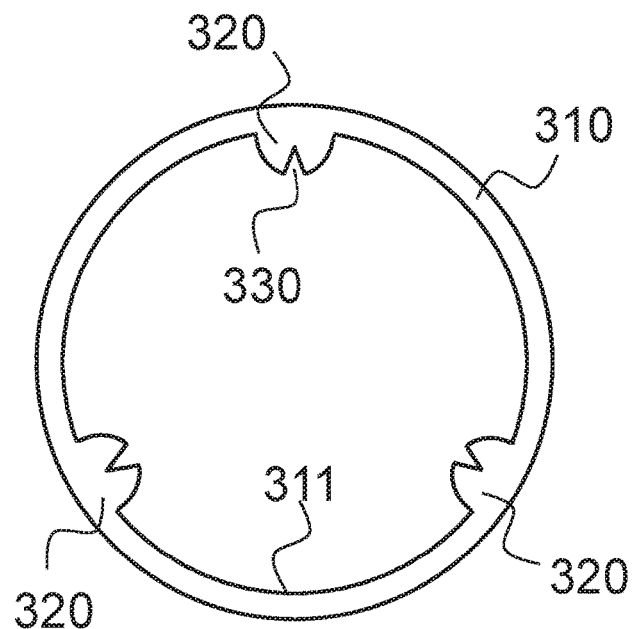
FIG. 3
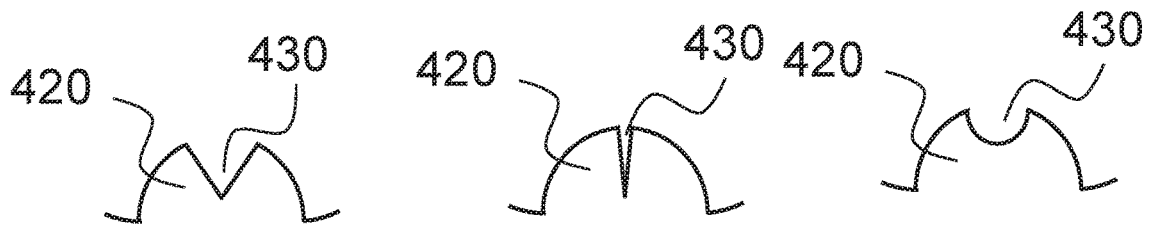
FIG. 4A    FIG. 4B    FIG. 4C
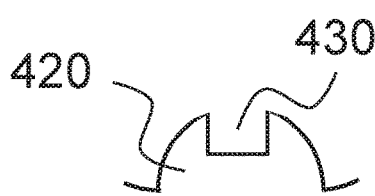 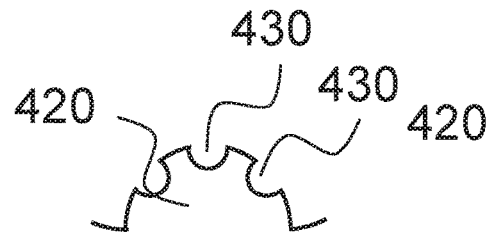 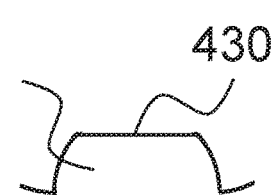
FIG. 4D    FIG. 4E    FIG. 4F

CONDUITS AND OTHER COMPONENTS WITH WICKING PROPERTIES AND ASSOCIATED METHODS

BACKGROUND

1. Field

The present disclosure generally relates to components for medical devices. More specifically, the present disclosure relates to conduits and other components providing humidified gases to and/or removing humidified gases from a patient, such as in positive airway pressure (PAP), respiratory, anesthesia, ventilator and insufflation systems.

2. Description of Related Art

In assisted breathing, particularly in medical applications, gases having high levels of relative humidity may be supplied and returned through conduits of a relatively restricted size. Condensation on the inside wall of the conduit is a frequent result of this high humidity. Condensation typically depends on many different factors such as, for example, the temperature profile in the conduit, the gas flow rate, the conduit's geometry, and the intrinsic "breathability" of the material (i.e. the ability of a material used in forming a part or all of a wall of a conduit to transmit water vapor through the wall to the environment outside of the wall, while substantially resisting transmission through the wall of the bulk flow of gas and any liquid water conveyed through the conduit) used to form the component.

In the prior art, attempts have been made to reduce the adverse effect of this condensation by reducing the level of condensation and/or providing collection points in the conduit for draining condensed liquid from the conduit, such as a water trap. Reducing the condensation has generally been by maintaining or elevating the temperature of the gases flow and/or of the conduit wall to reduce the formation of condensation.

While the above discussion is focused on conduits, similar comments apply to other components used in the transport of humidified gases. For example, patient interfaces and connectors such as wye piece connectors. Here to, there is the possibility of unwanted condensation and associated problems.

SUMMARY

According to a first aspect of the disclosure there is provided a medical circuit component for use with humidified gases, the medical circuit component comprising: a body comprising a wall having an inner surface that defines a space within which humidified gases may flow and/or be contained; and moisture transport means and/or element(s) at least partially coupled to and/or at least partially integrated into at least a part of said wall, the moisture transport means and/or element(s) being configured to receive moisture from vapors and/or liquid inside the space and transport at least some of said moisture away from where it was received.

The moisture transport means and/or element(s) may form at least a portion of the inner surface of the at least a part of the wall. The moisture transport means and/or element(s) may be completely coupled to or fully integrated with (or formed integrally with) the at least a part of the wall.

The moisture transport means and/or element(s) may comprise one or more elongate ribs and/or projections. The medical circuit component may have a major axis and the or one or more of the elongate ribs and/or projections may extend along at least a part of the length of the component along the major axis. The or one or more of said elongate ribs and/or projections may be parallel or substantially parallel to said major axis. The or one or more of said elongate ribs and/or projections may be linear or substantially linear, curved, arcuate, or helical.

The medical circuit component may comprise at least one cut-out or groove. The or at least one said cut-out or groove may provide at least in part said transport of at least some of said moisture away from where it was received. The or one or more of said elongate ribs and/or projections may comprise at least one said cut-out or groove. The or at least one cut-out or groove may extend along at least a portion of the length of the or one or more of the elongate ribs and/or projections. The or at least one said cut-out or groove may comprise one or more of: a slit, at least one narrow-mouthed V-shaped notch, a wide-mouthed V-shaped notch, a flat top surface, at least one semicircular notch, a rectangular notch or some other concave depression or form. The or one or more of the elongate ribs and/or projections may comprise a base portion adjacent said wall and the or at least one said cut-out or groove may be formed at or near said wall.

At least a portion of the medical circuit component may comprise and/or be formed from a breathable material that is permeable to water vapor but substantially impermeable to liquid water and bulk flow of gases inside the medical circuit component. The at least a portion of the medical circuit component may comprise at least a portion of said wall and/or at least a portion of said moisture transport means and/or element(s). The at least a portion may comprise said at least a portion of said wall and said at least a portion of said moisture transport means and/or element(s). The breathable material forming at least a portion of said wall may have a first porosity and a first permeability, said breathable material forming at least a portion of said moisture transport means and/or element(s) may have a second porosity and a second permeability, and the first porosity may be less than or equal to the second porosity and/or the first permeability is less than or equal to the second permeability. In some examples, the first porosity and/or the first permeability may be substantially zero. In other examples, the first porosity may be selected to substantially prevent transport of liquid through said at least a portion of said wall while maintaining structural integrity and flexibility of the medical circuit component. In further examples, the second porosity may be greater than the first porosity such that moisture absorption and transport may be increased at said at least a portion of said moisture transport means and/or element(s). In yet further examples, the second porosity may be selected such that said moisture transport means and/or element(s) may provide at least in part said transport of at least some of said moisture away from where it was received.

The medical circuit component may comprise at least one reinforcing rib and/or projection providing structural support to the body of the component. The or at least one said elongate rib and/or projection may comprise, at least in part, the or at least one reinforcing rib and/or projection. The reinforcing rib and/or projection and the body of the component may be made of a same or similar material. Using the same or a similar material may improve bonding. The porosity of the at least one reinforcing rib and/or projection may be less than a porosity of the one or more elongate ribs and/or projections.

The moisture transport means and/or element(s) may comprise one or more filaments. The or at least one of said filament may be at least partially coupled to and/or integrated into the body. The or at least one said filament may be completely coupled to or fully integrated with the wall. The one or more filaments may be at least partially coupled to and/or at least partially integrated into the one or more elongate ribs and/or projections. The or one or more of said filaments may comprise a foamed material. The one or more filaments may have a porosity greater than a porosity of the wall. The one or more filaments may have a porosity greater than a porosity of the elongate ribs and/or projections. The one or more filaments may have a melting point at least substantially higher than a melting point of the wall. The one or more filaments may have a melting point at least substantially higher than a melting point of the elongate ribs and/or projections.

The one or more filaments and the body of the component may be made of a same or similar material. Using the same or a similar material may improve bonding. The one or more filaments and the elongate ribs and/or projections may be made of a same or similar material. Using the same or a similar material may improve bonding. The one or more filaments and the wall may be made of different materials. The one or more filaments and elongate ribs and/or projections may be made of different materials. The one or more filaments may comprise at least a braid of at least one hydrophilic material. The one or more filaments may comprise and/or be formed from a breathable material. The one or more filaments may comprise a hollow body defining a channel therein that allows moisture to be transported away from where it was received by capillary action. The medical circuit component may comprise heating means to heat the one or more filaments.

Filaments may also be surface treated in the manners disclosed herein.

The medical circuit component may comprise heating means configured to heat the humidified gases and/or the wall. The heating means may be configured to heat the elongate ribs and/or projections.

The medical circuit component may comprise a corrugated or a straight conduit or may be a corrugated or a straight conduit. For the corrugated conduits at least a first portion of the one or more filaments may be secured in place by a wall forming the conduit and at least a second portion of the one or more filaments may be disposed within the space within which humidified gases may flow and/or be contained. More particularly, the at least a first portion of the one or more filaments may be secured in place by a portion of the corrugations forming the conduit, said portion comprising or being situated proximate to those parts of the conduit closest to a longitudinal axis of the conduit, i.e., at or proximate troughs in the corrugations when viewed from outside the conduit.

The medical circuit component may comprise one of or be a part of: an expiratory and/or an inspiratory tube in a dual limb circuit; a tube in a single limb circuit; a tube in a breathing circuit; a tube in an insufflation circuit; a tube in a surgical circuit; and a tube in an anesthesia circuit.

The medical circuit component may comprise or be part of a coaxial tube arrangement with one tube provided inside the other, the inner tube for conveying gases in a first direction and the space between the first and second tubes conveying gases generally in the opposite direction.

The medical circuit component may be configured to form at least in part a conduit.

The medical circuit component may comprise or be an inspiratory limb comprising a first connector to connect to an outlet of a humidification apparatus or chamber and/or a second connector to connect to a wye-piece or a patient interface.

The medical circuit component may comprise or be an expiratory limb comprising a first connector to connect to a wye piece or a patient interface and/or a second connector to connect to a gases source.

The medical circuit component may comprise at least one temperature probe and/or sensor or a port therefore. The at least one temperature probe and/or sensor may be coupled to and/or associated with the at least one connector disposed at one end of the medical circuit component to measure a gases temperature at or near a patient interface.

The medical circuit component may comprise three elongate ribs and/or projections equally spaced apart about a circumference of the inner surface of the wall.

According to a second aspect of the disclosure there is provided a system comprising: a medical circuit component comprising: a body including a wall having an inner surface that defines a space within which humidified gases may flow and/or be contained; and moisture transport means and/or element(s) at least partially coupled to and/or at least partially integrated (or formed integrally with) into at least a part of the wall, the moisture transport means and/or element(s) being configured to receive moisture from vapors and/or liquid inside the space and transport at least some of said moisture away from where it was received; and at least one or more of: a humidifier; and a gases source configured to be coupled to an inlet of a humidifier; and a patient interface configured to be connected to a patient.

The medical circuit component may be one or more of: an expiratory and/or an inspiratory tube in a dual limb circuit; a tube in a single limb circuit; a tube in a breathing circuit; a tube in an insufflation circuit; a tube in a surgical circuit; and a tube in an anesthesia circuit.

The medical circuit component may comprise or be part of a coaxial tube arrangement with one tube provided inside the other, the inner tube for conveying gases in a first direction and the space between the first and second tubes conveying gases generally in the opposite direction.

The medical circuit component may be a medical circuit component as defined in any one of the examples and embodiments of the first aspect.

According to a third aspect of the disclosure there is provided a system comprising: a medical circuit component comprising: a body including a wall having an inner surface that defines a space within which humidified gases may flow and/or be contained; and moisture transport means and/or element(s) at least partially coupled to and/or at least partially integrated (or formed integrally with) into at least a part of the wall, the moisture transport means and/or element(s) being configured to receive moisture from vapors and/or liquid inside the space and transport at least some of said moisture away from where it was received; and at least one or more of: means for humidifying gases; and means for delivering gases to the system; and means for delivering gases to a patient.

The medical circuit component may be one or more of: an expiratory and/or an inspiratory tube in a dual limb circuit; a tube in a single limb circuit; a tube in a breathing circuit; a tube in an insufflation circuit; a tube in a surgical circuit; and a tube in an anesthesia circuit.

The medical circuit component may comprise or be part of a coaxial tube arrangement with one tube provided inside the other, the inner tube for conveying gases in a first direction and the space between the first and second tubes conveying gases generally in the opposite direction.

The medical circuit component may be a medical circuit component as defined in any one of the examples and embodiments of the first aspect.

According to a fourth aspect of the disclosure there is provided a method of manufacturing a medical circuit component comprising: providing a body comprising a wall having an inner surface that defines a space within which humidified gases may flow and/or be contained; and providing moisture transport means and/or element(s) at least partially coupled to and/or at least partially integrated (or formed integrally with) into at least a part of the wall, the moisture transport means and/or element(s) being configured to receive moisture from vapors and/or liquid inside the space and transport at least some of said moisture away from where it was received.

The providing moisture transport means and/or element(s) may comprise forming one or more elongate ribs and/or projections on an inner surface of the wall, the one or more elongate ribs and/or projections extending along at least a part of the length of the component. The providing transport means and/or element(s) may further comprise forming at least one cut-out or groove within at least one of the or more of elongate ribs and/or projections. The at least one cut-out or groove may be formed by slicing off a top portion of the one or more of elongate ribs and/or projections or forming one or more of: a slit, a notch, at least one narrow-mouthed V-shaped notch, a flat top surface, a wide-mouthed V-shaped notch, at least one semicircular notch, a rectangular notch or some other concave depression or form within the one or more of elongate ribs and/or projections.

The body and the moisture transport means may be formed as a single extruded piece of a same material. The body and/or the moisture transport means may be formed using a foamed or a non-foamed breathable material.

Same material may include materials in the same family or of the same type, but with different material properties or subgroups.

The body and the moisture transport means may be co-extruded using different materials.

The providing transport means and/or element(s) may further comprise providing one or more filaments on an inner surface of the wall and/or within the elongate ribs and/or projections, the one or more filaments extending along at least a part of the length of the component.

The method may further comprise passing the medical circuit component into a corrugator to form a corrugated conduit. The providing one or more filaments may comprise securing at least a first portion of the one or more filaments to the one or more elongate ribs and/or projections and disposing at least a second portion of the one or more filaments within the space within which humidified gases may flow and/or be contained.

According to a fifth aspect of the disclosure there is provided a kit of parts for an unassembled medical system, the kit comprising: a medical circuit component comprising: a body including a wall having an inner surface that defines a space within which humidified gases may flow and/or be contained; and moisture transport means and/or element(s) at least partially coupled to and/or at least partially integrated (or formed integrally with) into said wall, the moisture transport means and/or element(s) being configured to receive moisture from vapors and/or liquid inside the space and transport at least some of said moisture away from where it was received; and, at least one or more of: a wye-piece; a humidification apparatus; and, an expiratory tube and/or an inspiratory tube.

The humidification apparatus may comprise or be a humidification chamber.

The medical circuit component may comprise a medical circuit component as defined in any one of the examples and embodiments of the first aspect.

According to a sixth aspect of the disclosure there is provided a conduit for use with humidified gases, the conduit comprising: a body comprising a wall having an inner surface that defines a space within which humidified gases may flow and/or be contained; and moisture transport means and/or element(s) at least partially coupled to and/or at least partially integrated (or formed integrally with) into at least a part of the wall, the moisture transport means and/or element(s) being configured to receive moisture from vapors and/or liquid inside the space and transport at least some of said moisture away from where it was received.

The moisture transport means and/or element(s) may form at least a portion of the inner surface of the at least a part of the wall. The moisture transport means and/or element(s) may be completely coupled to or fully integrated with (or formed integrally with) the at least a part of the wall.

The moisture transport means and/or element(s) may comprise one or more elongate ribs and/or projections. The conduit may have a major axis and the or one or more of the elongate ribs and/or projections may extend along at least a part of the length of the conduit along the major axis. The or one or more of said elongate ribs and/or projections may be parallel or substantially parallel to said major axis. The or one or more of said elongate ribs and/or projections may be linear or substantially linear, curved, arcuate, or helical.

The conduit may comprise at least one cut-out or groove. The or at least one said cut-out or groove may provide at least in part said transport of at least some of said moisture away from where it was received. The or one or more of said elongate ribs and/or projections may comprise at least one said cut-out or groove. The or at least one cut-out or groove may extend along at least a portion of the length of the or one or more of the elongate ribs and/or projections. The or at least one said cut-out or groove may comprise one or more of: a slit, a notch, at least one narrow-mouthed V-shaped notch, at least one semicircular notch, a wide-mouthed V-shaped notch, a flat top surface, a rectangular notch or some other concave depression or form. The or one or more of the elongate ribs and/or projections may comprise a base portion adjacent said wall and the or at least one said cut-out or groove may be formed at or near said wall At least a portion of the conduit may comprise and/or be formed from a breathable material that is permeable to water vapor but substantially impermeable to liquid water and bulk flow of gases inside the conduit. The at least a portion of the conduit may comprise at least a portion of said wall and/or at least a portion of said moisture transport means and/or element(s). The at least a portion may comprise said at least a portion of said wall and said at least a portion of said moisture transport means and/or element(s). The breathable material forming at least a portion of said wall may have a first porosity and a first permeability, said breathable material forming at least a portion of said moisture transport means and/or element(s) may have a second porosity and a second permeability, and the first porosity may be less than or equal to the second porosity and/or the first permeability is less than or equal to the second permeability. In some examples, the first porosity and/or the first permeability may be substantially zero. In other examples, the first porosity may be selected to substantially prevent transport of liquid through said at least a portion of said wall while maintaining structural integrity and flexibility of the conduit. In further examples, the second porosity may be greater than the first porosity such that moisture absorption and transport may be increased at said at least a portion of said moisture transport means and/or element(s). In yet further examples, the second porosity may be selected such that said moisture transport means and/or element(s) may provide at least in part said transport of at least some of said moisture away from where it was received.

The conduit may comprise at least one reinforcing rib and/or projection providing structural support to the body of the conduit. The or at least one said elongate rib and/or projection may comprise, at least in part, the or at least one reinforcing rib and/or projection. The reinforcing rib and/or projection and the body of the conduit may be made of a same or similar material. Using the same or a similar material may improve bonding. The porosity of the at least one reinforcing rib and/or projection may be less than a porosity of the one or more elongate ribs and/or projections.

The moisture transport means and/or element(s) may comprise one or more filaments. The or at least one of said filament may be at least partially coupled to and/or integrated into the body. The or at least one said filament may be completely coupled to or fully integrated with the wall. The one or more filaments may be at least partially coupled to and/or at least partially integrated into the one or more elongate ribs and/or projections. The or one or more of said filaments may comprise a foamed material. The one or more filaments may have a porosity greater than a porosity of the wall. The one or more filaments may have a porosity greater than a porosity of the elongate ribs and/or projections. The one or more filaments may have a melting point at least substantially higher than a melting point of the wall. The one or more filaments may have a melting point at least substantially higher than a melting point of the elongate ribs and/or projections. The one or more filaments and the body of the conduit may be made of a same or similar material. Using the same or a similar material may improve bonding. The one or more filaments and the elongate ribs and/or projections may be made of a same or similar material. Using the same or a similar material may improve bonding. The one or more filaments and the wall may be made of different materials. The one or more filaments and elongate ribs and/or projections may be made of different materials. The one or more filaments may comprise at least a braid of at least one hydrophilic material. The one or more filaments may comprise and/or be formed from a breathable material. The one or more filaments may comprise a hollow body defining a channel therein that allows moisture to be transported away from where it was received by capillary action. The conduit may comprise heating means to heat the one or more filaments.

The conduit may comprise heating means configured to heat the humidified gases and/or the wall. The heating means may be configured to heat the elongate ribs and/or projections.

The conduit may comprise or be a corrugated or a straight conduit. The conduit may be a corrugated tube and at least a first portion of the one or more filaments may be secured in place by the one or more elongate ribs and/or projections and at least a second portion of the one or more filaments may be disposed within the space within which humidified gases may flow and/or be contained.

The conduit may comprise one of or be a part of: an expiratory and/or an inspiratory tube in a dual limb circuit; a tube in a single limb circuit; a tube in a breathing circuit; a tube in an insufflation circuit; a tube in a surgical circuit; and a tube in an anesthesia circuit.

The conduit may comprise or be part of a coaxial tube arrangement with one tube provided inside the other, the inner tube for conveying gases in a first direction and the space between the first and second tubes conveying gases generally in the opposite direction.

The conduit may be an inspiratory limb comprising a first connector to connect to an outlet of a humidification apparatus or chamber and/or a second connector to connect to a wye-piece or a patient interface.

The conduit may an expiratory limb comprising a first connector to connect to a wye piece or a patient interface and/or a second connector to connect to a gases source.

The conduit may comprise at least one temperature probe and/or sensor or a port therefore. The at least one temperature probe and/or sensor may be coupled to and/or associated with the at least one connector disposed at one end of the conduit to measure a gases temperature at or near a patient interface.

The conduit may comprise three elongate ribs and/or projections equally spaced apart about a circumference of the inner surface of the wall.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present medical circuit component will now be described with reference to the accompanying drawings in which:

FIG. 3 is a simplified cross sectional view of a medical circuit component, constructed and operative in accordance with embodiments of the disclosure;

FIGS. 4A to 4I are simplified views illustrating different shapes/designs for the elongate ribs and/or projections of the medical circuit component of FIG. 3;

DETAILED DESCRIPTION

In the following description, numerous specific details are set forth in order to provide a thorough understanding of the various principles of the present invention. However, those skilled in the art will appreciate that not all these details are necessarily always required for practicing the present invention.

Condensation or rain-out can be a problem in the field of medical circuits, and in particular breathing circuits (including anesthetic circuits), where high humidity breathing gases come into contact with the walls of a component at a relatively lower temperature. In situations where condensation occurs, moisture has a tendency to pool in one spot. This could be due to the position of a conduit resulting in a bend or a low point that the water moves into. Another factor could be that condensation forms at one or more particular points in a conduit, such as a point where the conduit contacts a surface that is both cold and conductive or where the conduit contacts another surface that has a temperature lower than that of the conduit, resulting in that section of the conduit being cooled faster than other sections.

Pooling of moisture is undesirable for a multitude of reasons. Firstly, once moisture begins to pool it can move more easily and can end up in the patient interface, which is both uncomfortable and potentially dangerous to the patient. Alternatively, water can end up in equipment, such as a ventilator, resulting in damage to the equipment. Lastly, water could spill or flow out of the circuit, which would be unhygienic, particularly in a hospital setting.

In addition, moisture pooled in one location can be increasingly difficult to re-evaporate, particularly if the water pools at a location that caused it to condense in the first place. The inventors have recognized that moisture that is spread throughout the conduit, particularly to dryer and/or hotter regions, may re-evaporate more easily.

Figure 1:
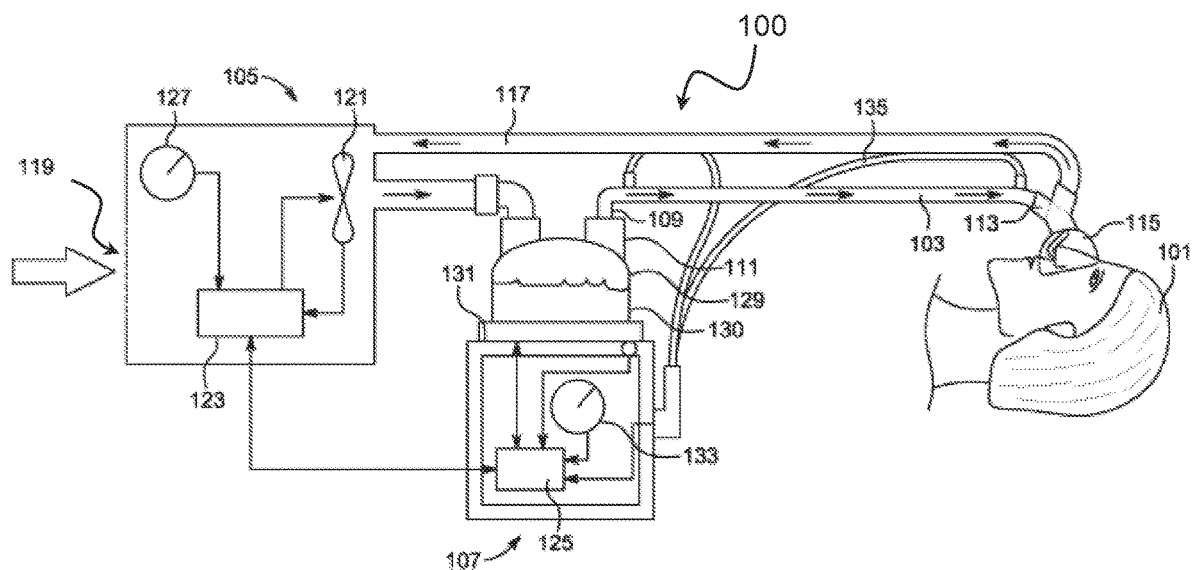
FIG. 1 is a schematic view of a breathing circuit including at least one medical circuit component, constructed and operative in accordance with at least one embodiment of the disclosure.

This can be achieved by providing wicking properties and/or other moisture transport mechanisms to a component of a medical circuit such as a conduit. This can provide benefits, particularly through more readily enabling condensed liquid to be re-evaporated (for example, by a greater contact with a heater and/or a greater surface area of liquid being exposed to a flow of gases thereover) and/or, where the component has a breathable wall, through increasing moisture contact (particularly surface area) with the breathable wall so as to increase the rate of moisture transmission through the wall. Absorption of water will reduce pooling on the inside of the conduit. Further, it assists in transporting moisture to the exterior surface of the conduit, from where it may be evaporated. The absorptive properties further spread out moisture not only through the wall from the interior surface towards the exterior surface but also along the wall. Thus, liquid water is spread out so that it creates less of restriction to flow inside of the conduit, and stops the seeding of further condensate. The present disclosure is therefore directed toward providing a medical circuit component, such as, for example, but not limited to, a conduit having moisture transport means and/or element(s) at least partially or fully coupled to and/or integrated (or formed integrally with) into a wall thereof. Reference is now made to FIG. 1, which is a schematic view of a breathing circuit comprising a medical circuit component, constructed and operative in accordance with at least one embodiment of the disclosure. The breathing apparatus 100 of FIG. 1 can be a continuous, variable, or bi-level positive airway pressure (PAP) system or provide some other form of respiratory therapy (e.g. high flow applications) or other forms of therapy completely. For example, the system may be used in surgical applications.

In the example breathing apparatus 100, a patient 101 receives humidified gas via an inspiratory tube. "Tube" is a broad term and is to be given its ordinary and customary meaning to a person skilled in the art (that is, it is not to be limited to a special or customized meaning) and includes, without limitation, cylindrical and/or non-cylindrical passageways formed from one or multiple parts or sections and may include connectors at the ends thereof and/or between different sections. An "inspiratory tube" is a tube that is configured to deliver humidified breathing gases to a patient.

Humidified gases can be transported in the breathing apparatus 100 of FIG. 1 as follows. Dry gases or ambient entrained gases pass from a gas source, such as for example, but not limited to, a ventilator/blower 105, to a humidifier 107, which humidifies the gases. The humidifier 107 connects to the inlet 109 (the end for receiving humidified gases) of the inspiratory tube 103 via a port 111, thereby supplying humidified gases to the inspiratory tube 103. The gases flow through the inspiratory tube 103 to the outlet (the end for expelling humidified gases), and then to the patient 101 through an inspiratory branch of a wye-piece 113 connected to the outlet and a patient interface 115. An expiratory tube 117 also connects to an expiratory branch of the wye-piece 113 and the patient interface 115. An expiratory tube is a tube that is configured to move exhaled or expelled gases away from a patient. Here, the expiratory tube 117 returns humidified gases, typically having a high humidity, from the patient interface 115 though the expiratory branch of the wye-piece 113 to the ventilator/blower 105.

Although shown as being connected to a wye-piece 113, it will be apparent to those skilled in the art that the tubes 103, 117 may be connected to the patient interface 115 (and/or other circuit components) in any suitable manner as long as the humidified gases can be transported in the breathing apparatus 100 from the humidifier 107 to the patient 101 and to the gas source 105. By way of non-limiting example, connectors (not shown) may be provided at one end or both ends of the inspiratory tube 103 and/or the expiratory tube 117 to couple the tubes 103, 117 with other circuit components. The inspiratory tube 103 may comprise a first connector at the inlet 109 to connect to the humidifier 107 at the port 111 and/or a second connector at the outlet to connect to the patient interface 115. Additionally, or alternatively, the expiratory tube 117 may comprise a first connector to connect to the patient interface 115 and/or a second connector to connect to the ventilator/blower 105. The connectors may further comprise any suitable sensors and/or probes (and/or ports for insertion or attachment thereof) to detect particular characteristic of the gases at a particular end of the tubes 103, 117 e.g. temperature sensor and/or probe.

Ambient or dry gases may enter the gas source 105 through a vent 119. A fan 121 can improve gases flow into the gas source (e.g., ventilator/blower) 105 by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed via a dial 127. It should be noted that the breathing apparatus 100 may be used with any suitable gases flow source that provides a gases stream to a patient 101 in use. For example, but not limited to, the gas source 105 could be replaced or supplemented by a wall port or a gas bottle.

The humidifier 107 may comprise a humidification chamber 129 configured to hold a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a heat-conductive base (for example, but not limited to, an aluminum base) contacting or associated with a heater plate 131 on the humidifier 107.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via dial 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as face and nasal masks), cannulas, nasal pillows, and an endotracheal tube. A patient interface usually defines a gases space which, when in use, receives warm humid breathing gases and is therefore at risk of condensation forming. Due to the close proximity of the patient interface 115 to the patient 101, this is very undesirable. To address the risk of condensation forming, a temperature probe 135 can connect to the inspiratory tube 103 near the patient interface 115, or to the patient interface 115. The temperature probe 135 monitors the temperature near the patient interface 115, or at the patient interface 115. A heating line (not shown) communicating with controller 125, for example, can be used to adjust the temperature in the patient interface 115 and/or inspiratory tube 103 to raise the temperature in the inspiratory tube 103 and/or patient interface 115 above the saturation temperature. In addition to (or as an alternative to) a temperature probe 135 and heating line, the patient interface 115 can also comprise a breathable interface.

In FIG. 1, exhaled or expelled humidified gases are returned from the patient interface 115 to the gas source 105 via the expiratory tube 117. The expiratory tube 117 preferably comprises a breathable foamed material (as explained in more detail below). However, the expiratory tube 117 can also be a medical tube as previously known in the art, such as those made from non-breathable material. The expiratory tube 117 may also comprise breathable material that is extruded or wrapped and is non-foamed. In any case, the expiratory tube 117 may or may not have a temperature probe and/or heating line, as described above with respect to the inspiratory tube 103, integrated with it or provided therein or thereabout to reduce the risk of condensation forming. Furthermore, the expiratory tube 117 need not return exhaled or expelled gases to the gas source 105. Alternatively, exhaled or expelled humidified gases can be passed directly to ambient surroundings or to other ancillary equipment, such as an air scrubber/filter (not shown). In certain embodiments, the expiratory tube is omitted altogether.

As will be apparent to those skilled in the art, the expiratory 117 and/or inspiratory 103 tubes may be any suitable type of conduits such as, for example, but not limited to, corrugated or straight tubes (e.g., tubes having a smooth bore and/or a smooth wall). The tubes 103, 117 may further comprise any suitable form of heating means such as, for example, but not limited to, heating wires or heating lines, provided within the gases flow passageway or within or about the tube wall, to reduce or eliminate the formation of condensation within the tube, and to maintain a substantially uniform temperature or other desired temperature profile of the gases as they flow through the tube in use.

In some embodiments, the tubes 103, 117 may be made of a breathable material such as a breathable thermoplastic polymer that allows water vapor to pass through the material. Hereinafter, throughout the description, a material that allows the passage of water vapor (or liquid water absorbed into the wall) through the wall to the outer surface of the tube without allowing the bulk passage of liquid water or bulk flow of respiratory gases from inside the wall to ambient is described as a "breathable" material. Materials may be breathable due to their composition, physical structure or a combination thereof. Preferably, the breathable thermoplastic material is a foamed or non-foamed polymer elastomer (or TPE as defined by ISO 18064:2003(E)), such as a copolyester thermoplastic elastomer (e.g., ARNITEL®, which is a copolyester thermoplastic elastomer with a polyether soft segment, or other TPC or TPC-ET material as defined by ISO 18064:2003(E)), or a polyether block amide (e.g., PEBAX®, which is a polyamide thermoplastic elastomer with a polyether soft segment, or other TPA-ET materials as defined by ISO 18064:2003(E)), or a thermoplastic polyurethane (TPU material as defined by ISO 18064:2003(E)), or a foamed polymer blend, such as TPE/polybutylene terephthalate (PBT, e.g., DURANEX® 500FP) blend. If the breathable thermoplastic polymer is a foamed TPE/PBT blend, the blend preferably comprises between 80% and 99% (or about 80% and 99%) TPE by weight and 20% and 1% (or about 20% and 1%) PBT by weight. In any of the above embodiments, the void fraction of the foamed material can be greater than 25% (or about 25%), such as between 25 and 60% (or about 25 and 60%), or between 30 and 50% (or about 30 and 50%). In at least one embodiment, no more than 5% (or about 5%) of the voids of said foamed material exceed a diameter of 500 µm. In the embodiments where the tubes 117/103 are made of a foamed polymer, the foamed polymer may have an outer skin layer of closed cell voids, that allow for the transmission of water vapor but substantially prevent the transmission of liquid vapor and bulk flow of gases. Examples of tubes and materials for such tubes are disclosed in WO2011/077250, the content of which is incorporated by reference herein.

For non-foamed, breathable embodiments, conduits can for example be formed by extrusion or by helically winding and joining adjacent winds of a strap or strips of breathable material. Such methods and arrangements are described in EP1153627, the content of which is incorporated by reference herein.

Figure 10:
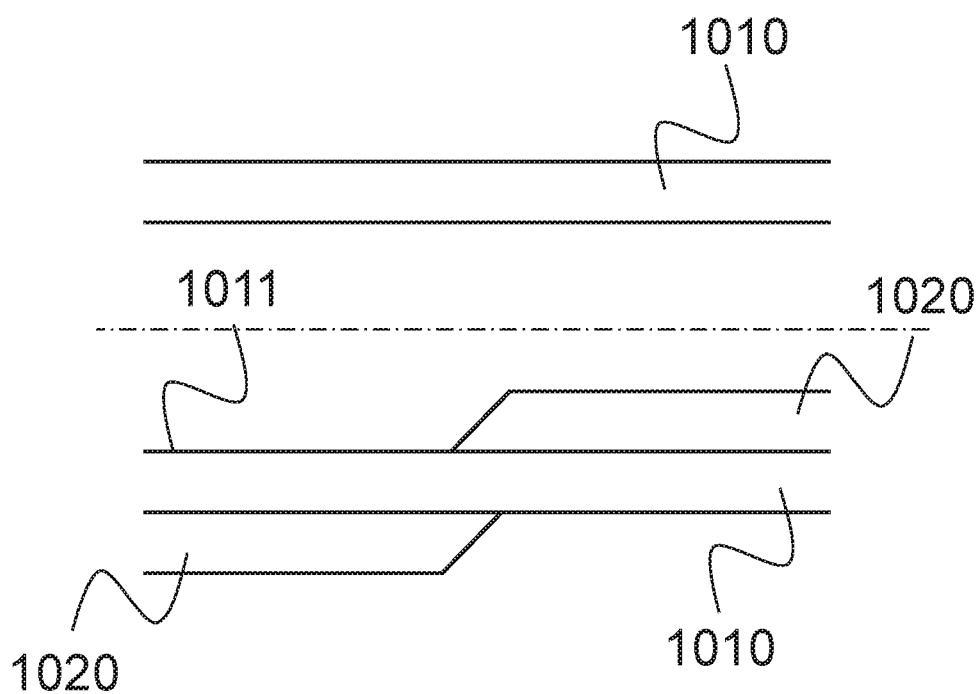

The tubes 103, 117 may further comprise one or more reinforcing members such as one or more structural ribs and/or projections arranged about the enclosing wall. The one or more reinforcing members may additionally or alternatively be provided within or joined to a surface of the wall, such as a thickened wire element. These reinforcing members can provide crush resistance, while leaving the tube wall flexible enough to permit short-radius bends without kinking, occluding or collapsing. The reinforcing members may be positioned on an inner wall and/or an outer wall of the tubes 103, 117. In some configurations, at least some of the reinforcing members may be positioned on an inner wall of the tubes 103, 117 and may comprise at least a portion partially positioned on the outer wall of the tubes 103, 117. Additionally, or alternatively, at least some of the reinforcing members may be positioned on an outer wall of the tubes 103, 117 and may comprise at least a portion partially positioned on the inner wall of the tubes 103, 117. For example, as shown in FIG. 10, an elongate rib and/or projection 1020 may extend in part along an outer surface of the tube 1010, extend through the tube wall and then extend along an inner surface 1011 of the tube 1010. Repeating this may result in a generally serpentine pattern. The ribs and/or projections may be arranged parallel to the longitudinal axis therefrom, linear but offset or have some other profile such as arcuate or helical about the tube. Alternatively, different lengths of the ribs and/or projections may be provided respectively on inner and outer surfaces of the tube without passing through the tube wall. An advantage of having the ribs on the inner wall is to provide a more uniform outer surface/wall. In addition, providing a groove on the inner wall at a location where a reinforcing member is positioned on the outer wall can ease drawing moisture. Conversely, an advantage of having the ribs on the outer wall is to provide a less obstructed, a more uniform gas flow path and an easier manufacturing process of the tubes. Preferably, the reinforcing members run longitudinally along the length of at least a portion of an inner wall of the tubes 103, 117. These reinforcing members can be extruded or co-extruded with the tube to be generally aligned with the longitudinal axis of the tube.

Figures 11A, 11B:
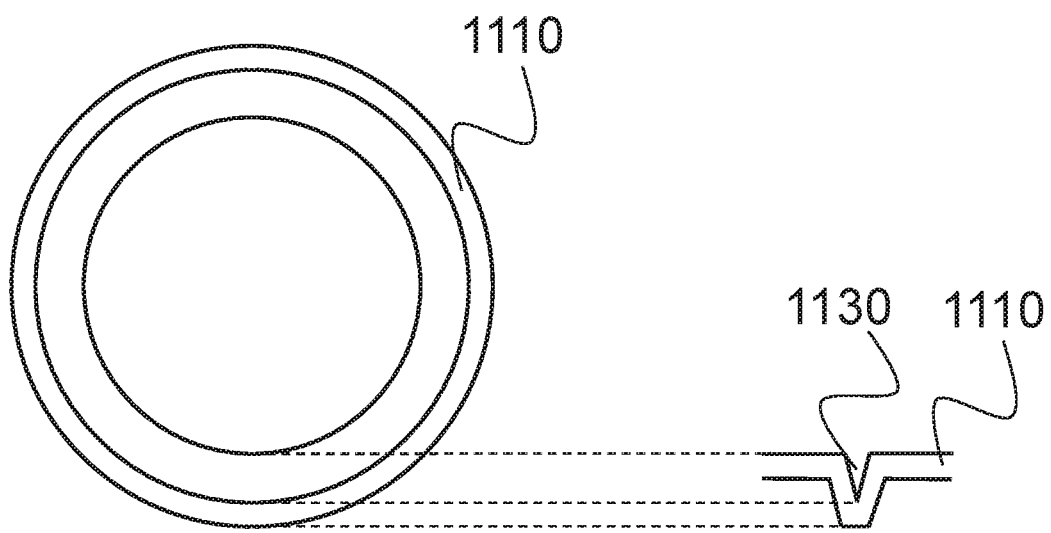
Figure 11C:
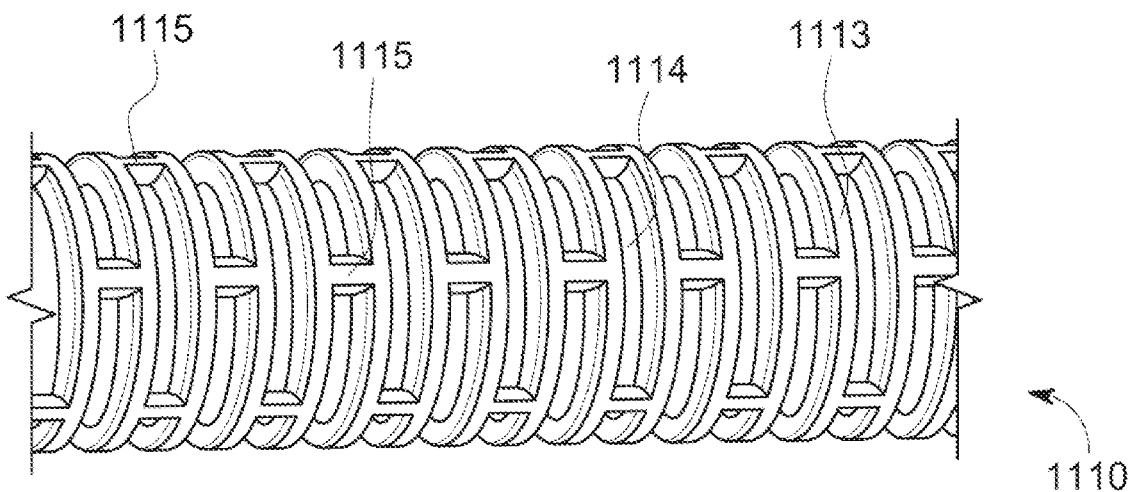

In some embodiments, the expiratory tube 117 and/or the inspiratory tube 103 may comprise moisture transport means and/or element(s) at least partially coupled to and/or at least partially integrated (or formed integrally with) into a wall of the tubes 103, 117, preferably an inner surface thereof, configured to receive moisture from vapors and/or liquid inside the gases flow passageway and transport at least some of the moisture away from where it was received. The wicking means and/or elements may be provided as part of the structure of the tubes 103, 117 and/or may be coupled to or fully integrated with an inner wall of the tubes 103, 117. Having wicking means and/or elements coupled to and/or integrated into the structure of a tube allow for quicker and easier manufacture as a separate wicking element would not need to be manufactured and added to the tube. For example, the wicking means and/or elements may include one or more features disposed on an inner wall and allowing moisture to be transported, preferably longitudinally (e.g. along a major axis) along the length of at least a portion of the tubes 103, 117. For example, the wicking means may be arranged or configured such that moisture is transported along a length of a portion of the tubes 103, 117 in a linear or spiral manner. Additionally, or alternatively, the wicking means may include features that allow for wicking in a circumferential direction. Circumferential wicking means and/or element(s) may also be used to connect separate sections of longitudinal wicking means and/or element(s) that are not longitudinally aligned. FIGS. 11A-11B illustrate an exemplary embodiment where circumferential wicking is provided. For example, the circumferential wicking is provided by a groove or a narrow corrugation 1130 formed on the body of the tube 1110. Water from condensation may be therefore be wicked circumferentially up the sides of the tube 1110. This may create a tortuous wicking path preventing moisture to flow to the lowest point within the tubes. This may also expose the condensate to more surface area than a straight wicking path. The misaligned wicking means (i.e. sections of the longitudinal wicking means and/or element(s) that are not longitudinally aligned) may be different in number, shape, location, material, material properties, and/or rotational orientation, along the length of the tubes 103, 117. This may have the additional advantage of being able to address localized issues and/or prevent/reduce forces caused by high frequency ventilation being translated from one end of the tube 103, 117 to the other (mechanical wave propagation). In other words, movement/displacement of the tube 103, 117 caused by a pulsatile gas delivery under high frequency ventilation can be prevented/reduced. As an alternative to misaligned ribs and/or projections, a dam may be provided to some or all of the wicking means to prevent, inhibit, or slow the transport of moisture through large distances along the wicking path (as this may encourage pooling of moisture in lower areas of the tubes), while still allowing for localized spreading and re-evaporation of moisture along the wicking path. For example, but not limited to, the dam may be a partial or total break in the wicking means and/or element(s). In the embodiments comprising one or more grooves, the dam may be formed in a groove such that moisture is totally or partially blocked along the groove. Additionally, and/or alternatively, the wicking means may comprise the one or more reinforcing members. FIG. 11C shows an exemplary tube 1110 where dams 1115 are provided. FIG. 11C shows an outer surface of a tube 1110 comprising peaks 1113 and troughs 1114. Each peak 1113 is coupled to an adjacent peak 1113 via one or more dams 1115. Although not shown in FIG. 11C, it will be apparent that the troughs 1114 provided on the outer surface of the tube 1110 correspond to peaks on the inner surface of the tube 1110. Similarly, the peaks 1113 (including the dams 1115) provided on the outer surface of the tube 1110 correspond to troughs on the inner surface of the tube 1110. FIG. 11C shows that each peak 1113 is connected to an adjacent peak 1113 by a plurality of dams 1115. The plurality of dams 1115 connecting a particular peak 1113 to adjacent peaks 1113 on the outer surface are not aligned which results in the creation of a tortuous path within the tube 1110 (i.e., formed by the corresponding troughs on the inner surface of the tube 1110) such that transport of moisture is prevented, inhibited or at least slowed down.

Although the above embodiments have been described in relation to expiratory or inspiratory tubes forming part of a breathing circuit, those skilled in the art will appreciate that the wicking means or element(s) may be integrated into the structure of any medical circuit component, or portion of such component, in which condensation is undesirable. The disclosed wicking means and/or element(s) can be incorporated into a variety of conduit components, including expiratory and/or inspiratory limbs in a dual limb circuit, a conduit in a single limb circuit, etc. and are suitable for use in a variety of medical circuits, including but not limited to insufflation, anesthesia, and breathing circuits. They may be additionally or alternatively be used in connectors such as cuffs, catheters and wye-piece connectors, and/or in patient interfaces. For example, the wicking features and/or element(s) may be provided on the inner, patient-facing side of a full face mask, nasal mask, or in a cannula.

For example, the wicking means and/or elements described hereinabove and hereinafter can be integrated into the structure of a component of an insufflation or smoke evacuation system. An insufflation system may include an insufflator that produces a stream of insufflation gases at a pressure above atmospheric for delivery into the patient abdominal or peritoneal cavity. The gases pass into a humidifier, including a heater base and humidifier chamber, with the chamber in use in contact with the heater base so that the heater base provides heat to the chamber. In the humidifier, the insufflation gases are passed through the chamber so that they become humidified to an appropriate level of moisture. The insufflation system may include a delivery conduit that connects between the humidifier chamber and the patient peritoneal cavity or surgical site. The conduit has a first end and second end, the first end being connected to the outlet of the humidifier chamber and receiving humidified gases from the chamber. The second end of the conduit is placed in the patient surgical site or peritoneal cavity and humidified insufflation gases travel from the chamber, through the conduit and into the surgical site to insufflate and expand the surgical site or peritoneal cavity. The system may also include a controller that regulates the amount of humidity supplied to the gases by controlling the power supplied to the heater base. The controller can also be used to monitor water in the humidifier chamber. A smoke evacuation system can lead out of the body cavity of the patient.

The smoke evacuation system can be used in conjunction with the insufflation system described above or may be used with other suitable insufflation systems. The smoke evacuation system may comprise a discharge or exhaust limb, a discharge assembly, and a filter. The discharge limb connects between the filter and the discharge assembly, which in use is located in or adjacent to the patient surgical site or peritoneal cavity. The discharge limb is a self-supporting tube (that is, the tube is capable of supporting its own weight without collapsing) with two open ends: an operative site end and an outlet end. The gases supplied by the insufflation system may already be humidified at the point of entry to the patient body cavity. As the body cavity is already moist and humid, the gases do not tend to lose moisture in the body, and can become fully saturated if they are not already at saturation point. If the gases are dry on entry to the body cavity, they tend to become humidified as they pass through the body cavity, picking up moisture from the damp atmosphere in the body cavity above the internal organs.

Figure 2:
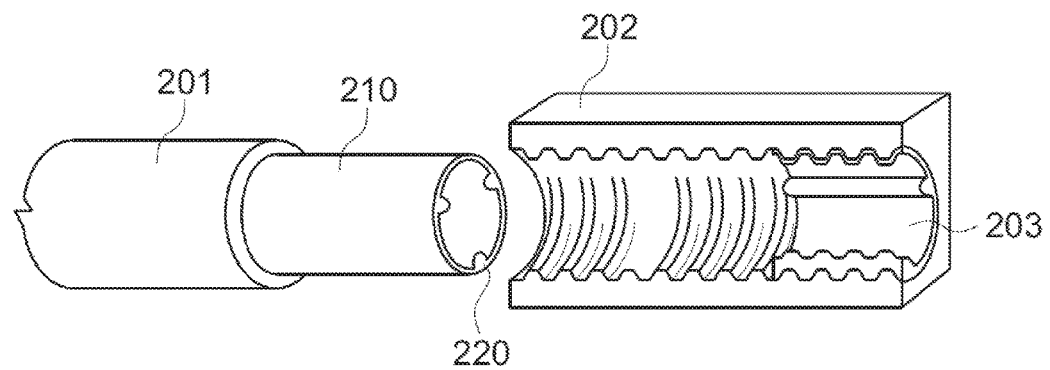
FIG. 2 is a schematic side view showing an apparatus that may be used to manufacture a medical circuit component according to at least one embodiment of the disclosure.

Reference is now made to FIG. 2, which shows apparatus that may be used to manufacture a medical circuit component according to at least one embodiment of the disclosure. In some embodiments, the conduit 210 (as shown) may be formed as a single extruded piece having elongate ribs and/or projections 220 on an inner wall. The form/shape of the elongate ribs and/or projections is determined by the extruder die head 201. The conduit 210 may be formed as a straight tube or may be fed to a carrugator 202 to form a corrugated tube 203. In other embodiments, some or all of the elongate ribs and/or projections 220 can be made of material different from the material of the wall and the conduit 210 may be formed by co-extrusion. In further embodiments, some or all of the elongate ribs and/or projections 220 may be formed separately and added to an inner and/or outer surface of the conduit wall to form the conduit 210.

Additionally, and/or alternatively, the conduit 210 may be further processed to provide or include wicking means or additional wicking means such as, for example but not limited to, one or more filaments thereby improving the wicking properties of the conduit 210. In one example, some or all of the elongate ribs and/or projections 220 disposed on the inner surface of the conduit wall may be processed so as to form a cut-out, or groove, or a concave depression as it will be described hereinafter with reference to FIGS. 3 and 4A to 4I. In another example, the inner surface of the conduit wall may be processed so as to form a cut-out, or groove, or a concave depression at a location where an elongate rib and/or projection is disposed on the outer surface of the conduit wall. Such a cut-out or groove may extend through the section of the conduit wall and into at least of portion of the inner side of the elongate rib and/or projection. In further examples, one or more filaments may be added to the inner wall of the conduit and/or to at least one of the elongate ribs and/or projections 220 disposed on the inner wall as it will be described hereinafter with reference to FIG. 9. According to some embodiments, such filament(s) may at least in part be provided in cut-outs or grooves.

Although FIG. 2 shows a conduit 210 being formed by extrusion, those skilled in the art will appreciate that this example is provided for illustration only and is not limiting. In one example, the conduit 210 may be made using a foamed breathable material formed as a single extruded piece having elongate ribs and/or projections 220 on an inner wall. The form/shape of the elongate ribs and/or projections 220 is determined by the extruder die head 201, and the size and foaming level is controlled by the temperature and pressure when it exits the die head 201. In another example, the conduit 210 may be formed using a film, such as a breathable film, and a reinforcing member. Each of the film and the reinforcing member are spirally wound around a mandrel to form the conduit 210. Any manufacturing processes and materials suitable to form a foamed or non-foamed breathable conduit, or a foamed or non-foamed non-breathable conduit may be used to form the conduit 210 described hereinafter in the different embodiments.

Additionally, the conduit 210 may be surface modified by either post-processing, co-extruding a coating, or adding a surface modifying material, for example, to the master batch or extrudate for foamed or non-foamed conduits. The surface modifying material may be hydrophilic and/or hydrophobic, and may be added to one or more locations in the conduit 210. For example, it may be added to the elongate ribs and/or projections 220, but not the wall of the conduit 210, or vice versa, or added to both. In another example, at least one portion of the conduit 210 and/or at least one portion of the elongate ribs and/or projections 220 may comprise a first surface modifying agent, while at least another portion of the conduit 210 and/or elongate ribs and/or projections 220 may comprise a second surface modifying agent. A surface modifying agent may preferably comprise glycerol monostearate (GMS), ethoxylated amine, alkanesulphonate sodium salt, or lauric diethanolamide. Preferably the surface modifying agent comprises at least about 0.05, 0.1, 0.15, 0.2, 0.25, 0.3, 0.35, 0.4, 0.45, 0.5, 1.1, 1.2, 1.3, 1.4, or 1.5 weight percent (wt. %) of the total extrudate. More preferably the surface modifying agent comprises about 0.25 wt. % of the total extrudate. More preferably the surface modifying agent comprises about 0.5 wt. % of the total extrudate.

For example, MLDNA-418 supplied by Clariant (New Zealand) Ltd. and under the product name "418 LD Masterbatch Antistatic" is a surface modifying agent master batch with 5(±0.25) % glycerol monostearate (CAS No. 123-94-4) as an active ingredient.

A surface modifying agent may additionally be included in the extrudate. Such an agent assists in increasing the surface energy (or the wettability) of the surface of the formed elongate rib and/or projection 220 and/or conduit 210. In this manner, advantageously increasing the surface energy may act to promote reduced contact angles between drops or beads of condensate or liquid that may build up on the surface.

The contact angle is the angle formed by the solid surface of the elongate rib and/or projection 220 and/or conduit 210 and the tangent line to the upper surface at the end point of a liquid droplet. Contact angle measurement is a non-destructive method of determining the wetting behavior of liquids on a solid surface. It enables the calculation of surface and interfacial tension along with spreading coefficients. The surface tension calculated from the contact angle data is a characteristic measurement for the respective surface and fluid system.

The contact angle between a liquid and a surface is measured using a goniometer (angle measurement device). A precise volume of the liquid is dispensed on the cleaned and dried flat test surface using a precision syringe. The droplet is allowed to stabilize for a few seconds and a high magnification camera is used to capture the image of the droplet. The image is digitized and the angle between the test surface and the tangent line along the droplet surface is measured.

Reducing contact angle increases contact area between the droplet and solid surface, and also reduces droplet thickness, enhancing heat conduction through the droplet. Both effects increase droplet evaporation rate.

Increasing the energy of a surface reduces contact angle of a droplet placed on the surface. In this manner, a droplet of liquid on the surface of a higher energy surface can preferentially have a greater surface area in contact with the surface, a surface of relatively lower energy.

Advantageously, the droplet may be spread across a larger surface area of the surface and, therefore, be more likely to re-evaporate into the gas stream flowing over the elongate rib and/or projection 220 through the conduit 210. For example, the droplet or bead may spread across the internal surface of the wall of the elongate rib and/or projection 220 and/or conduit 210, allowing greater surface area for re-evaporation (in a heated tube) into the passing gas stream. In an unheated tube, having the droplet or bead being spread across the internal surface of the wall of the elongate rib and/or projection 220 and/or conduit 210, allows greater absorption of moisture by the wall of the conduit thereby reducing condensation within the conduit.

In another example, where the conduit 210 is corrugated (whether as an annular corrugate or spiral corrugate form), droplets or beads of water are more likely to form in a part of the corrugation in a low temperature position (i.e. generally this is a part of the corrugation closest to or most exposed to ambient conditions surrounding the conduit 210). In such a case, altering the surface properties of the conduit surface can promote a droplet or bead formed at the low temperature position to spread across the conduit surface and in doing so may move towards a region of warmer temperature. Such migration of movement of the droplet or bead can allow for further improved re-evaporation rates, both due to the droplet possibly moving toward regions of warmer temperatures, as well as possibly toward regions of the tube which are exposed to greater or faster gas stream flows. Greater re-evaporation rates may therefore be achieved by providing for improved migration of a droplet or bead radially inward from the internal surface wall of the conduit 210.

Reference is now made to FIG. 3, which is a cross sectional view of a medical circuit component constructed and operative according to embodiments of the disclosure. The conduit 310 may be made using a breathable material and formed as a single extruded piece. The conduit 310 may comprise a tubular body having inner wall 311 defining a gases flow passageway for humidified gases. The conduit 310 may further comprise one or more elongate ribs and/or projections 320 disposed on the inner wall 311 and running longitudinally and/or extending along the length of at least a portion of the conduit 310. In a foamed embodiment, the inner wall or inner surface 311 of the conduit 310 may comprise a skin of closed cell voids that reduces moisture absorption and/or transport radially through the inner wall. In order to provide the wicking properties to the conduit 310 (i.e. allowing water or moisture to be wicked along the length of at least a portion of the conduit), the one or more elongate ribs and/or projections 320 may undergo a post extrusion process that exposes the inner cell voids and allows for increased moisture absorption and/or transport.

In a foamed embodiment, the inner cell voids may be exposed by slicing off the top of one or more of the elongate ribs and/or projections 320. In another embodiment, cell voids may be exposed by forming one or more grooves 330 into one or more of the elongate ribs and/or projections 320.

FIG. 3 shows an exemplary medical circuit component 310 comprising three ribs and/or projections 320 positioned on the inner surface of the wall and equally spaced apart about the circumference of the medical circuit component 310, which may be foamed or un-foamed. A V-shaped groove 330 is formed into each rib and/or projection 320 of the conduit 310 thereby exposing the inner cell voids and allowing moisture to be absorbed and/or transported. Non-limiting examples of shapes/designs for the grooves 330 and the ribs and/or projections 320 are illustrated in FIGS. 4A to 4I, where:

- FIG. 4A depicts a wide-mouthed V-shaped notch (with a mouth length equal to or wider than the length of its sidewalls or depth);
- FIG. 4B depicts a slit;
- FIG. 4C depicts a semi-circular groove;
- FIG. 4D depicts a rectangular groove;
- FIG. 4E depicts multiple semi-circular grooves;
- FIG. 4F depicts a rib and/or projection having a flat top surface;
- FIG. 4G depicts cut-out portions or narrow-mouthed V-shaped notches adjacent to the inner surface of the wall (with a mouth length less than the length of its sidewalls or depth); and,
- FIGS. 4H and 4I depicts a plurality of cut-out portions or narrow-mouthed V-shaped notches.

Although three elongate ribs and/or projections 320 are shown in FIG. 3, those skilled in the art will appreciate that any number of elongate ribs and/or projections 320 may be provided and processed to form the moisture means and/or element(s). The number of ribs and/or projections 320 may be determined based on the properties to be given to the medical circuit component 310 in terms of breathability, flexibility, strength, average porosity (i.e. average porosity of a conduit wall that may have a gradient porosity defined between an inner wall (e.g. very porous) and an outer wall (e.g. substantially non-porous: 0% or near 0%) the average porosity is related to void fraction and percentage of open cells versus closed cells), and moisture transport. For example, providing too many ribs and/or projections 320 may limit the remaining wall surface area, lower breathability, and may render the medical circuit component 130 overly stiff. On the other hand, having a single rib and/or projection 320 may cause the medical circuit component 310 to bend as it cools and having two ribs and/or projections 320 may allow bending along a first axis while preventing bending on a second axis. Also, it will be apparent that the elongate ribs and/or projections 320 shown in FIG. 3 may be of any suitable shape such as linear or substantially linear, curved or arcuate, helical, etc. and may be parallel or substantially parallel to the major axis of the conduit 310. Alternatively, the wick profiles shown in FIGS. 4A-I may be formed directly into the wall of the conduit (without being formed on a rib and/or a projection).

In embodiments where the conduit 310 is made of a porous breathable material, the wicking means may be at least partially provided by the porosity of the material. The wicking properties of the conduit 310 may be further improved by increasing the porosity of the elongate ribs and/or projections 320. The porosity influences the speed at which moisture is absorbed and/or transported through a material, and relates to both cell void fraction and cell void size of the material. Therefore, in some embodiments, the conduit 310 may be manufactured such that a first porosity is obtained for the tubular body and a second porosity is obtained for the elongate ribs and/or projections 320. For example, the material used for the tubular body may have a porosity low enough to substantially prevent transport of liquid through the material while the elongate ribs and/or projections 320 may be manufactured with an increased porosity, e.g., the material may be selected such that open cell voids may be formed on an outer surface of the elongate ribs/or projections 320. This would result in increased porosity of the elongate ribs and/or projections 320 while maintaining the structural integrity of the conduit 310. Cell voids may be formed during a foaming stage, which begins once the breathable material leaves the die head (e.g. die head 201 of FIG. 2) and stops once the breathable material is cooled to a point where the forces of bubble expansion are lower than the forces required to deform the molten polymer. The conduit 310 may then be cooled once it enters the corrugator (202 of FIG. 2), the outer surface of the tubular body being cooled faster than the inner surface thereby allowing the breathable material more time to form more and/or larger cell voids at the reinforcing members 320.

Additionally, and/or alternatively, the wicking means and/or elements may comprise the one or more grooves 330 which provide wicking at least partially by capillary action. Forming one or more grooves 330 into the elongate ribs and/or projections 320 provides a thin path that may be configured to transport moisture via capillary action. The capillary wicking may be provided in addition to the porous wicking described in the above embodiments. Alternatively, this capillary wicking may be implemented without the porous wicking in embodiments where the tubular body of the conduit 310 is made of a non-breathable and/or non-foamed material. This capillary wicking is caused by the force of adhesion between the fluid and the surface, and by the surface tension of the fluid. The wicking effect may also be affected by external forces, such as gravity when moisture is traveling vertically. As the positioning of the conduit 310 may not be controllable and moisture tends to pool in lower areas of the conduit 310, the capillary forces would need to be sufficient to wick moisture a substantial distance against the gravity force.

Improving the wicking properties of the conduit 310 may be achieved by varying or altering the dimensions and/or shape of the grooves 330. In some embodiments, a groove may extend as far as possible into an elongate rib and/or projection to increase the surface area and the cross-sectional area of the groove. The depth may be limited by the size of the elongate rib and/or projection and the thickness of the tubular body of the conduit 310. Hence, the depth of the grooves 330 formed into the elongate ribs and/or projections 320 may be defined such that the structural and pneumatic integrity of the conduit 310 is maintained.

In some embodiments, the grooves 330 may be relatively narrow in comparison to the depth in order to maintain a high surface area to volume ratio (as illustrated in FIG. 4B for example). For capillary wicking, such a configuration increases the speed at which moisture is transported along a groove and the height and/or distance on which the moisture can be transported. For porous wicking, such a configuration facilitates the manufacturing process as less material needs to be removed from the groove. It also leaves a larger amount of porous material on the elongate rib and/or projection thereby improving the porous wicking capacity.

In some embodiments, the grooves 330 may be relatively wide in comparison to the depth (as illustrated in FIG. 4A, 4C or 4D for instance). Having a wider groove provides benefits in the volume of moisture that can be removed though capillary wicking. Although the speed may not be as fast as a thin groove, the increased cross-section of the groove may provide a greater overall flow rate. This could be particularly useful in redistributing larger pools of moisture, where the overall flow rate may be more important than speed and/or distance of the overall wicking. For porous wicking, a larger groove would allow for greater moisture exchange between the elongate rib and/or projection and the gases flow passageway. Such a configuration would be beneficial in both absorbing moisture more quickly and making moisture more available for re-evaporation.

Figure 4G:
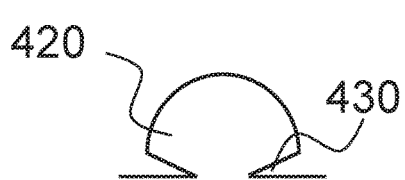
Figure 4H:
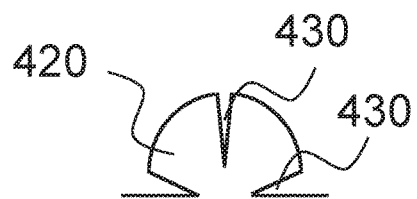
Figure 4I:
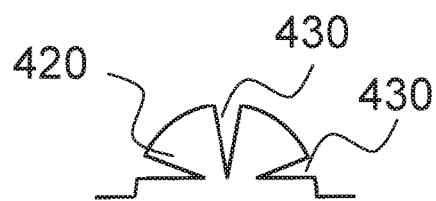

In some instances, water droplets may not be able to be received in notches and/or grooves that are too narrow (e.g., FIG. 4B) and/or may not be able to break-up and travel in grooves being too large/flat (e.g., FIG. 4D). Therefore, in some embodiments, the grooves 330 may have sharp edges as illustrated in FIGS. 4B, and 4G to 4I. Sharp edges may be beneficial to improve travel of water along the wicking means as water has a certain surface tension and adheres more readily to certain sizes or shapes of grooves. FIGS. 4G to 4I illustrate exemplary embodiments where the grooves comprise sharp edges to improve movement/travel of water by capillary action:

FIG. 4G depicts grooves 430 formed as cut-out portions or narrow-mouthed V-shaped notches (i.e., sharp edges) into a base of the rib/projection adjacent to the inner surface of the wall. These cut-outs or notches can be provided on both sides of the base as close as possible to the wall. One advantage of this design is that water at/near the wall can soak into the cut-out portions or notches thereby improving the capillary wicking. Another advantage is that these grooves 430 could be formed by extrusion through an appropriate shaped die head, and may not need post-processing. Alternatively, the grooves 430 may be formed by post processing after extrusion; and, FIGS. 4H and 4I depict ribs and/or projections comprising a plurality of grooves 430 formed as cut-out portions or narrow-mouthed V-shaped notches (i.e., sharp edges). FIG. 4H is similar to FIG. 4G but shows the rib and/or projection further comprising a V-shaped notch similar to the one of FIG. 4B. FIG. 4I is similar to the design of FIG. 4H. In this example however the cut-out portions or V-shaped notches are not formed as close as possible to the wall but rather they are formed into the rib and/or projection at a certain distance from the wall. Although three sharp edges grooves are illustrated in FIGS. 4H-4I, it will be apparent to those skilled in the art that more than three grooves can be provided.

In some embodiments, the conduit may be manufactured by extrusion/co-extrusion with a die-head designed to form the rib/projections of FIGS. 4H-4I. Alternatively, the conduit may be formed and then post-processed to form the rib/projections of FIGS. 4H-4I.

As explained hereinabove, the different dimensions and/or shapes of the grooves 330 provide different advantages in terms of capillary and/or porous wicking. Therefore, in some embodiments, the conduit 310 may comprise different grooves 330 designs on different elongate ribs and/or projections 320. Additionally, or alternatively, the conduit 310 may comprise grooves 330 of varying lengths, shapes, locations, materials, material properties, and/or rotational orientations, along the length of the conduit 310. For example, the groove 330 of FIG. 4A may be provided on a first elongate rib and/or projection while the groove 330 of FIG. 4D may be provided on a second elongate rib and/or projection. In another example, the groove 330 of FIG. 4A may be provided on a first elongate rib and/or projection while the groove 330 of FIG. 4D may be provided on a second elongate rib and/or projection, and the first and second elongate ribs and/or projections may not be longitudinally aligned. Circumferential wicking means and/or element(s) may then be used to connect these separate sections so as to create a tortuous wicking path preventing moisture to flow to the lowest point within the conduit 310. This may also expose the condensate to more surface area than a straight wicking path. Having misaligned elongate ribs and/or projections may have the additional advantage of being able to address localized issues and to prevent wave propagation along the conduit 310 under high frequency ventilation. As an alternative to misaligned elongate ribs and/or projections, a dam may be provided to prevent, inhibit, or slow the transport of moisture through large distances along the wicking path (as this may encourage pooling of moisture in lower areas of the tubes), while still allowing for localized spreading and re-evaporation of moisture along the wicking path. For example, but not limited to, the dam may be a partial or total break in the wicking means and/or element(s). In the embodiments comprising one or more grooves, the dam may be formed in a groove such that moisture is totally or partially blocked along the groove. In the embodiments comprising a filament or an elongate rib and/or projection with porous wicking properties, the dam may be formed as a section of the filament or elongate rib and/or projection with reduced wicking properties, or no wicking properties at all. Alternatively, the dam may be provided as a gap in the filament or elongate rib and/or projection. Those skilled in the art will appreciate that any suitable combination may be implemented in order to achieve different wicking properties for a particular conduit.

Figure 5A:
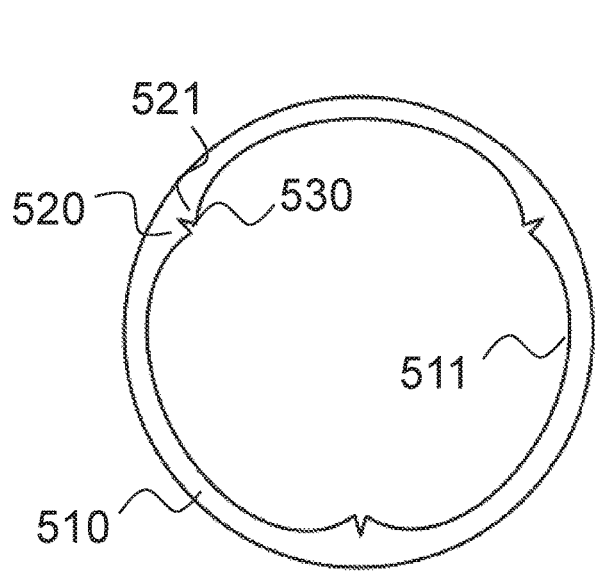
FIGS. 5A-5B are simplified views of a medical circuit component, constructed and operative in accordance with other embodiments of the disclosure.
Figure 5B:
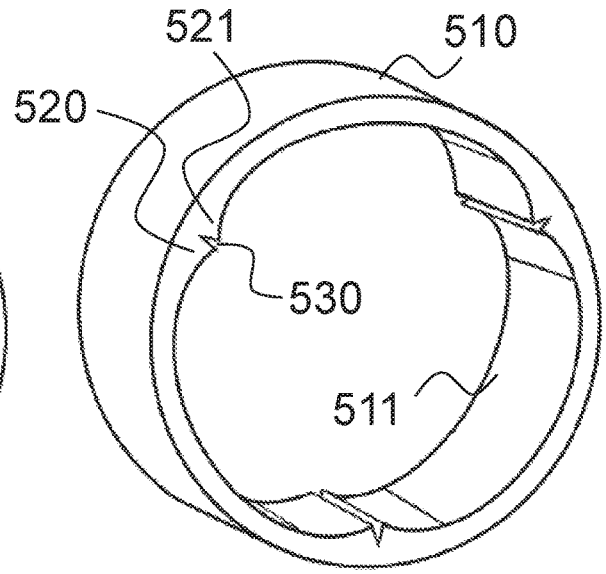

Reference is now made to FIGS. 5A-5B, which are views of a medical circuit component constructed and operative according to embodiments of the disclosure. The conduit 310 may comprise a tubular body having inner wall 511 defining a gases flow passageway for humidified gases. The conduit 510 may further comprise elongate ribs and/or projections 520, 521 disposed on the inner wall 511 and running longitudinally and/or extending along the length of at least a portion of the conduit 510. In some embodiments, the elongate ribs/projections 520, 521 may be provided close to each other such that the space between them form a sharp-edge groove 530. To do so, the conduit 510 may be formed as a single extruded piece and the extruder die tip may be cut such that the sharp-edge(s) is/are formed during the extrusion process. The space/sharp-edge groove 530 formed between the elongate ribs and/or projections 520, 521 provides at least in part the transport of at least some of the moisture away from where it was received.

Figure 6:
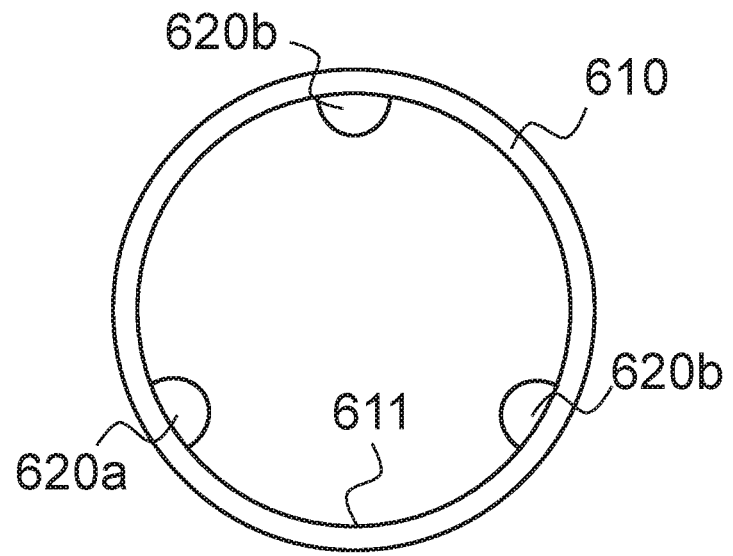
FIG. 6 is a simplified cross sectional view of a medical circuit component, constructed and operative in accordance with other embodiments of the disclosure.

Reference is now made to FIG. 6, which is a simplified cross sectional view of a medical circuit component constructed and operative in accordance with other embodiments of the disclosure. FIG. 6 shows a conduit 610 comprising a tubular body and elongate ribs and/or projections 620a, 620b disposed on an inner wall or surface 611. The elongate ribs and/or projections 620a, 620b may be formed by a co-extrusion process using a material different from the material used to form the tubular body of the conduit 610. Co-extruding the elongate ribs and/or projections 620a, 620b has the advantage of using a material that may not be suitable to form the conduit 610. However, the material selection may be limited if the elongate rib and/or projection 620a, 620b is configured to provide structural support to the tubular body of the conduit 610. Therefore, in some embodiments, the elongate ribs and/or projections 620a, 620b may be separated into structural reinforcing members 620a and non-structural reinforcing members 620b. The elongate ribs and/or projections 620a may provide structural support to the tubular body of the conduit 610 in terms of crush resistance, (preventing kinking, occluding or collapsing while leaving the tube wall flexible enough to permit short-radius bends), and for axial reinforcement against stretching (particularly longitudinal stretching). They may be made of the same material or a material from the same family of materials as the tubular body of the conduit 610 in order to improve bonding. Same or similar material may include materials in the same family or of the same type, but with different material properties or subgroups.

Further, these structural reinforcing members 620a may be made of any suitable material (foamed breathable material, un-foamed breathable material, foamed non-breathable material, or foamed non-breathable material) and may have any of the porous wicking properties described hereinabove in relation to the elongate ribs and/or projections of FIGS. 3 to 5B.

The elongate ribs and/or projections 620b that do not only provide structural reinforcement may be made of any suitable material (foamed breathable material, un-foamed breathable material, foamed non-breathable material, or un-foamed non-breathable material) and may wick moisture through any porous wicking process described hereinabove in relation to the elongate ribs and/or projections of FIGS. 3 to 5B. In addition, a wider range of materials may be available for selection. In foamed embodiments, the material may be selected to allow for a different void fraction and/or void size during the formation of the cell voids without having to be limited to materials configured to maintain pneumatic and structural integrity of the tubular wall of the conduit 610. In some embodiments, the elongate ribs and/or projections 620b may be formed using materials having void fraction and/or void size greater than the ones for the elongate ribs and/or projections 620a providing structural reinforcement, thereby improving the porous wicking efficiency.

Additionally, and/or alternatively, the elongate ribs and/or projections 620b may not comprise an outer skin layer of closed cell voids that allow for the transmission of water vapor but substantially prevent the transmission of liquid vapor and bulk flow of gases. In this embodiment, the material for the elongate ribs and/or projections 620b may be selected for its tendency to form open cell voids on an outer surface. This would allow for absorption of moisture through all exposed surfaces of the elongate ribs and/or projections 620b thereby improving moisture transfer between the elongate ribs and/or projections 620b and the gases flow passageway. Another advantage of using such material is that no additional processing may be needed to expose the cell voids.

Additionally, and/or alternatively, one or more of the elongate ribs and/or projections 620a, 620b may be processed to form one or more grooves (not shown in FIG. 6) as described hereinabove in relation to the elongate ribs and/or projections of FIGS. 3 to 5B. Forming one or more grooves into the elongate ribs and/or projections 620a, 620b allows moisture to be wicked by capillary action and improves the overall wicking properties of the conduit 610. In foamed embodiments, this may also assist the porous wicking in situations where the elongate ribs and/or projections 620a, 620b are formed using materials forming open cell voids on an outer surface. Also, the one or more grooves may increase the surface area of the elongate ribs and/or projections 620b thereby allowing a quicker exchange of moisture with the gases flow path.

Figure 7:
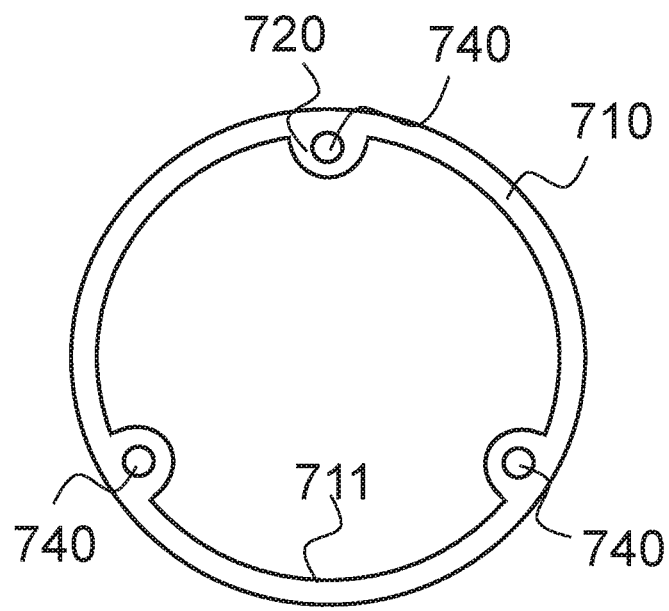
FIG. 7 is a simplified cross sectional view of a medical circuit component, constructed and operative in accordance with other embodiments of the disclosure.

Reference is now made to FIG. 7, which is a simplified cross-sectional view of a medical circuit component constructed and operative in accordance with embodiments of the present disclosure. FIG. 7 illustrates a conduit 710 comprising one or more filaments 740 that can be at least partially or fully coupled to and/or integrated into the inner wall or surface 711. The one or more filaments may, for example but not limited to, comprise a thread-like structure or be made of a thread or thread-like material. The one or more filaments may for example comprise a fiber or a bundle of fibers. The fiber(s) may be natural or synthetic. Preferably, the one or more filaments 740 run longitudinally along the length of at least a portion of the conduit 710. The one or more filaments 740 facilitate absorption and transport of moisture. In some embodiments, the one or more filaments 740 may be at least partially or fully coupled to and/or integrated into the elongate ribs and/or projections 720 disposed on the inner wall 711 of the conduit 710. The one or more filaments 740 may be adapted to follow to any wicking path e.g. linear or substantially linear, curved or arcuate, helical, etc. and may be parallel or substantially parallel to the major axis of the conduit 710. The elongate ribs and/or projections 720 may be any type of elongate ribs and/or projections described hereinabove in the different embodiments.

The one or more filaments 740 may be added to the conduit 710 during the extrusion process. This may be achieved by co-extruding the one or more filaments 740 so that they are located within the elongate ribs and/or projections 720 once the material of the conduit 710 has cooled down. Preferably, the one or more filaments 740 may be made of a material having a melting point at least substantially higher than the melting point of the material used to form the conduit 710 so that the one or more filaments 740 do not melt during the extrusion process. For semi-crystalline polymers, the melting point may be defined as the point at which the crystalline structure unstacks or unfolds. For amorphous polymers, the melting point may be defined as the temperature or range of temperatures (above the glass transition temperature) at which the material viscosity reduces enough to be managed with a traditional extrusion process. The one or more filaments 740 may be made of a material from the same family of materials used to form the tubular body of the conduit 710 in order to improve bonding. In other embodiments, the one or more filaments 740 may be made of a material that prevents bonding with the elongate ribs and/or projections 720. For example, the one or more filaments 740 may be made from a braid of hydrophilic material (e.g. cotton). The braid may cause the formation of gaps between the one or more filaments 740 and the elongate ribs and/or projections 720 thereby facilitating wicking along the length of at least a portion the one or more filaments 740. Two or more materials may be braided or otherwise joined into a composite fiber or filament to achieve the wicking functionality provided by the one or more filaments 740.

Additionally, and/or alternatively, the one or more filaments 740 may be made at least partially from a breathable polymer similar to the ones described hereinabove. The polymer may be substantially more porous than the wall of the conduit 710 to allow for transport of moisture. The one or more filaments 740 may further comprise a hollow channel running along their lengths enabling moisture to be transported by capillary action.

Additionally, and/or alternatively, the one or more filaments 740 may include one or more grooves on an outer surface. The one or more grooves may be dimensioned small enough to prevent ingress of the conduit material during the manufacturing process, but large enough to allow water ingress and transport.

In addition, various filaments configured to transport moisture are disclosed in US2004/0118401, the content of which is incorporated in its entirety by reference herein, and may be used with embodiments of the disclosure. For example, the one or more filaments 740 may be comprised of an outer hydrophilic layer, covering an inner insulating hydrophobic layer, which in turn covers a heater element. Condensation/Water is attracted to and drawn into the hydrophilic layer, and is then re-vaporized as it is heated by the heater element. The intermediate hydrophobic insulating layer may be provided to electrically insulate the inner heater element from the rest of the system. Such filaments 740 may be constructed by coextruding the hydrophobic insulating layer and hydrophilic layer onto a heater wire. Suitable materials for the hydrophilic layer include polyester or polyurethane foam, or a braid of hydrophilic material e.g. cotton. Suitable materials for the hydrophobic insulating layer include polypropylene or silicone coatings. Alternatively, the one or more filaments 740 may include a looped back heater element, coated in a hydrophobic insulating layer, and the whole encased within a hydrophilic surrounding layer. In a further variation, the heater element may be an electrical resistance heater and includes a length of higher resistance and a length of lower resistance, insulated from one another and joined at their remote ends. In a still further variation, the one or more filaments 740 may be disposed in the conduit 710 as a simple loop. Each of these variations provide both ends of the heated wick at the same end of the conduit, allowing a single connection of the heater element to an energizing source. Alternatively, the hydrophilic layer may achieve its hydrophilic (water attracting effect), through its physical structure and capillary action rather than an inherent property of the material composition. The hydrophilic layer may be constructed from a hydrophilic material composition or alternatively may be constructed from water resistant materials but have a physical structure configured so water 'soaks' into or is attracted to the layer through capillary action. In some embodiments, the hydrophilic layer may be made of a braided sheath. The braided filaments may be may be of a water resistant material such as polyethylene terepythalate (PET), polyethylene or polypropylene. In use, liquid water or condensate is drawn into the spaces between the filaments of the braided sheath by capillary action thus giving layer a water attracting or hydrophilic effect. In other embodiments, the hydrophilic layer may be constructed from a water resistant material (for example PET) and may attract water into spaces and voids on the outer surface of the layer through capillary action. The hydrophilic layer may be formed from a partially foamed plastic layer which encases the insulated conductive wire(s). The outer layer may be covered in voids or pores, in order that the heated wick can attract water to itself through capillary action. Alternatively, the outer layer may be formed by sintering. Heater element(s) may be imbedded in layer, and may also include an electrical insulating layer. In further embodiments where the hydrophilic layer is not braided, the outer layer may include a number of grooves and/or fins in order to allow the wick to attract water though capillary action. The grooves may be substantially axial, annular, helical or knurled in a crisscross fashion.

Figure 8A:
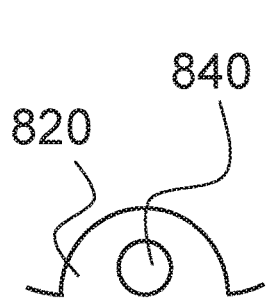
FIGS. 8A to 8C are simplified views illustrating different shapes and/or designs for the elongate ribs and/or projections of the medical circuit component of FIG. 6.
Figure 8B:
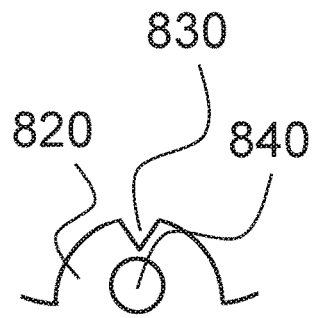
Figure 8C:
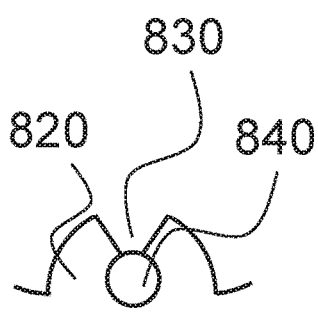

The conduit 710 is further designed such that water is sufficiently absorbed by the one or more filaments 740 in areas where condensate is pooling, and sufficiently exposed in areas where re-evaporation may occur. This may be achieved using any one of the embodiments described herein such as, forming one or more grooves into an elongate rib and/or projection, or co-extruding an elongate rib and/or projection with open cell voids, etc. Non-limiting examples of medical circuit components incorporating one or more filaments are illustrated in FIGS. 8A to 8C. FIG. 8A shows an elongate rib and/or projection 820 comprising a filament 840. The elongate ribs and/or projections 820 may be made of a material having a porosity greater than the porosity of the conduit wall. In foamed embodiments, the moisture may therefore travel through the open cell voids of the elongate ribs and/or projections 820 to be absorbed and transported by the filament 840. FIG. 8B shows an embodiment where a groove 830 (e.g. V-shaped notch) is formed in the elongate rib and/or projection 820. Open cell voids may therefore be exposed by the groove 830 thereby facilitating radial porous wicking of moisture through the elongate rib and/or projection 820 to the filament 840. Longitudinal wicking may then be achieved by the filament 840. Additionally, and/or alternatively, the groove 830 may be formed so as to expose an outer surface of the filament 840 as shown in FIG. 8C. One advantage of providing one or more filaments 840 on an inner wall of the conduit 810 is that longitudinal wicking is improved which in turn facilitates redistribution of moisture along the length of the conduit. Although the design features described hereinabove facilitate absorption of moisture in areas of high condensation, those skilled in the art will appreciate that these features may work in reverse to allow exposure and re-evaporation of moisture in drier sections of the tube.

Figure 9:
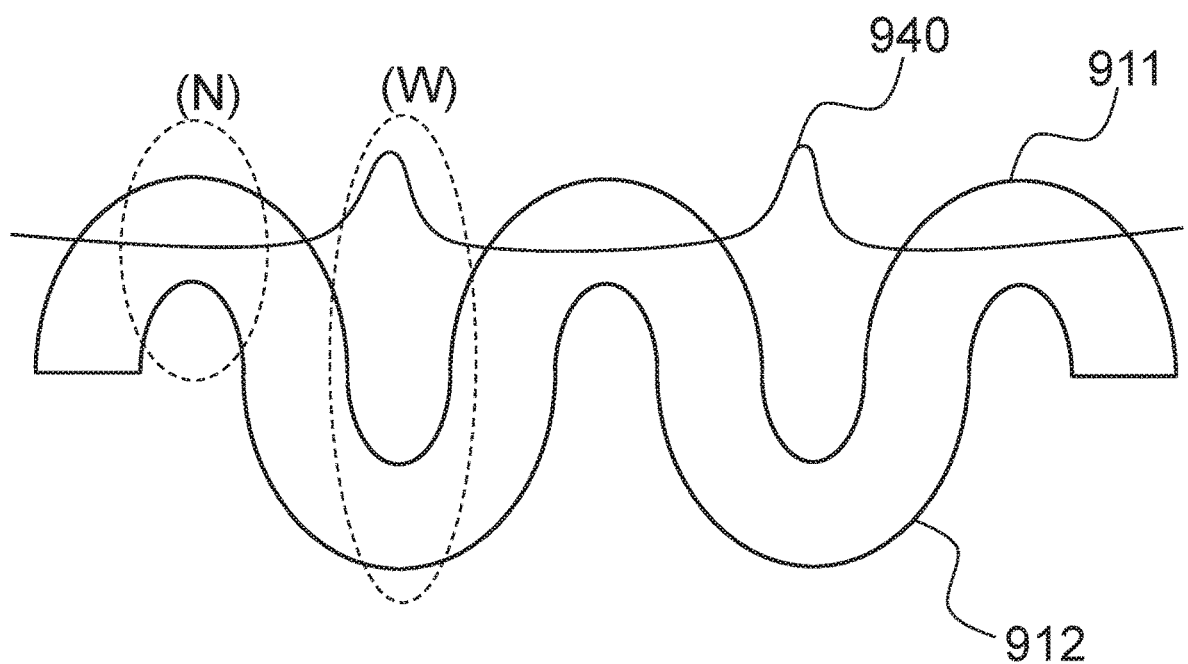
FIG. 9 is a schematic cross sectional view of a medical circuit component, constructed and operative according to embodiments of the disclosure; and, FIG. 10 is schematic cross sectional view of a medical circuit component, constructed and operative according to embodiments of the disclosure; and, FIGS. 11A-11C are schematic views of a medical circuit component constructed and operative according to embodiments of the disclosure.

Reference is now made to FIG. 9, which is a partial side cross sectional view of a medical circuit component constructed and operative in accordance with embodiments of the present disclosure. It will be understood that FIG. 9 is not to scale and illustrates only one sidewall of a corrugated conduit 910, the other side wall not being depicted for the sake of clarity. FIG. 9 shows a partial sidewall of a corrugated conduit 910 comprising an inner wall 911, an outer wall 912, and a filament 940. The corrugated conduit 910 may be configured to regularly expose the filament 940 to the gases flow passageway. This may be achieved during the manufacturing process by pulling the filament 940 straight while the elongate ribs and/or projections follow the contours of the corrugations. Additionally, or alternatively, the filament 940 may be a stretchable filament or enough slack in the filament 940 may be provided so as to allow bending of the conduit 910. Once formed, the filament 940 may be exposed to the gases flow passageway when the corrugations result in the conduit 910 being at its widest (section W). This exposure allows rapid transfer of moisture between the gases passageway and the filament 940 and also facilitates both absorption in areas of pooled condensate and re-evaporation in dryer areas. Additionally, the filament 940 may be secured in place by passing through the elongate rib and/or projection (not pictured) disposed on the inner wall 911 when the corrugations result in the conduit 910 being at its narrowest (section N).

Wicking Properties

TABLES 1-2 show some example properties of different samples prepared in accordance with some embodiments described hereinabove. The samples have been prepared to illustrate the effect/impact of the different materials and/or designs on the wicking properties.

TABLE 1 illustrates the wicking properties of different foamed samples prepared with different percentages of a chemical or physical foaming agent (Clariant HYDROCEROL® BIH-10E). Samples 1-2, 3-4, and 5-6 have been prepared with respectively 0, 5 and 8% by weight of foaming agent BIH-10E. In addition, samples 1, 3, and 5 comprise a single cut along their lengths while samples 2, 4, and 6 comprise a V-shaped groove of about 0.5 mm cut along the length of the wall. In summary, TABLE 1 shows the following samples:

Sample 1—single cut/0% foaming agent;
Sample 2—V-shaped groove of about 0.5 mm/0% foaming agent;
Sample 3—single cut/5% foaming agent;
Sample 4—V-shaped groove of about 0.5 mm/5% foaming agent;
Sample 5—single cut/8% foaming agent; and,
Sample 6—V-shaped groove of about 0.5 mm/8% foaming agent.

A water bath (about 100 ml of water mixed with about 3 ml of food colouring/dye) was prepared in a container with a water depth of approximately 8 mm. For each sample, the following test was carried out: (i) weigh the sample; (ii) dip the sample in the water bath for one minute with the sample contacting the bottom of the container; (iii) remove the sample from the water bath and remove any water droplets from the bottom 8 mm of the sample; and, (iv) measure the weight of the sample and the distance along the cut/groove the dye wicked up the sample. The results are shown in TABLE 1 below

| Sample | 1 | 2 | 3 | 4 | 5 | 6 |
|---|---|---|---|---|---|---|
| Foaming level (%) | 0 | 0 | 5 | 5 | 8 | 8 |

| Sample | 1 | 2 | 3 | 4 | 5 | 6 |
|---|---|---|---|---|---|---|
| Void fraction (%) | 4.83 | 4.83 | 43.16 | 43.16 | 51.55 | 51.55 |
| Cut type | Single narrow cut lengthways | Groove of approx. 0.5 mm | Single narrow cut lengthways | Groove of approx. 0.5 mm | Single narrow cut lengthways | Groove of approx. 0.5 mm |
| Width (mm) | 10.3 | 12.33 | 16.6 | 16.98 | 20.27 | 20.31 |
| Length (mm) | 92.05 | 82.84 | 74.89 | 72.28 | 76.93 | 69.4 |
| Thickness (mm) | 2.8 | 3.4 | 5.02 | 5.08 | 6.91 | 6.67 |
| Test length (minutes) | 1 | 1 | 1 | 1 | 1 | 1 |
| Weight with holder before test (g) | 3.005 | 4.503 | 3.581 | 3.914 | 4.898 | 4.268 |
| Weight with holder after test (g) | 3.01 | 4.507 | 3.589 | 3.927 | 4.909 | 4.282 |
| Change in weight (g) | 0.005 | 0.004 | 0.008 | 0.013 | 0.011 | 0.014 |
| Dye travel distance (mm) | 44 | 44.4 | 10.23 | 34.6 | 12.38 | 22.3 |
| Total distance travelled (−8 mm water depth) | 36 | 36.4 | 2.23 | 26.6 | 4.38 | 14.3 |
| Total distance travelled × Change in weight (mm · mg) | 180 | 145.6 | 17.84 | 345.8 | 48.18 | 200.2 |

The results show that samples with 0% foaming agent traveled far with both cut types but had the least changes in weight of all the foaming percentages. This distance is acceptable but in some instances more weight may be preferable so that liquid can continue traveling along the cut/groove. The wicking efficacy may be defined as the combination of weight change and distance traveled (although each of these independently may additionally or alternatively be used as a measure of wicking efficacy) and is indicated, for each tested sample, in the last row of TABLE 1. It therefore appears that, for the 5% and 8% foamed samples, the 0.5 mm V-shaped groove has better wicking efficacy than the single narrow cut. As explained hereinabove, this is due to the V-shape of the groove which provides an improved capillary action compared to a narrow cut. For the non-foamed samples, the 0.5 mm V-shaped groove produced an increase in distance traveled but the change in weight was reduced as compared to the single cut sample, resulting in lower overall wicking efficacy. However, the provision of the V-shaped groove may still be of benefit, solely through generating the increased distance traveled.

TABLE 2 illustrates the wicking properties of different samples with different grooves being cut into a rib/projection on a wall. All samples shown in TABLE 2 were prepared with a 5% foaming agent. In TABLE 2:

Sample 1 corresponds to the groove shown in FIG. 4A;
Sample 2 corresponds to the groove shown in FIG. 4B;
Sample 3 corresponds to the groove shown in FIG. 4D;
Sample 4 corresponds to the groove shown in FIG. 4F;
Sample 5 corresponds to the groove or cut-out shown in FIG. 4G with surface treatment (treated with corona discharge); and,
Sample 6 corresponds to the groove or cut-out shown in FIG. 4G without surface treatment.

The methodology explained hereinabove in relation to the samples of TABLE 1 has been followed. The results are shown in TABLE 2 below

| | Sample | | | | | | | | |
|---|---|---|---|---|---|---|---|---|---|
| | Control 1 (no rib, no cut) | Control 2 (no rib, no cut) | Control 3 (rib, no cut) | 1 | 2 | 3 | 4 | 5 | 6 |
| Foaming level (%) | 0 | 5 | 5 | 5 | 5 | 5 | 5 | 5 | 5 |
| Weight with holder before test (g) | 2.911 (no holder) | 2.880 (no holder) | 4.587 (no holder) | 4.722 | 5.26 | 4.905 | 5.336 | 5.397 | 5.047 |

-continued

| | Sample | | | | | | | | |
|---|---|---|---|---|---|---|---|---|---|
| | Control 1 (no rib, no cut) | Control 2 (no rib, no cut) | Control 3 (rib, no cut) | 1 | 2 | 3 | 4 | 5 | 6 |
| Weight with holder after test (g) | 2.914 (no holder) | 2.883 (no holder) | 4.594 (no holder) | 4.73 | 5.279 | 4.926 | 5.36 | 5.416 | 5.06 |
| Cut Type (FIG.) | None | None | None | 4A | 4B | 4D | 4F | 4G | 4G |
| Width (mm) | 8.92 | 14.07 | 29.16 | 24 | 25 | 25 | 25 | 27 | 26 |
| Length (mm) | 100 | 100 | 100 | 100 | 100 | 100 | 100 | 100 | 100 |
| Thickness (mm) | 2.84 | 4.52 | 2.46 | 2 | 2 | 2 | 2 | 2 | 2 |
| Test length (minutes) | 1 | 1 | 1 | 1 | 1 | 1 | 1 | 1 | 1 |
| Change in weight (mg) | 3 | 3 | 7 | 8 | 19 | 21 | 24 | 19 | 13 |
| Dye travel distance (mm) | 8 | 8 | 8 | 8 | 49.25 | 21.42 | 10.46 | 38.57 | 45.06 |
| Total distance travelled (−8 mm) | 0 | 0 | 0 | 0 | 41.25 | 13.42 | 2.46 | 30.57 | 37.06 |
| Total distance travelled × Change in weight (mm · mg) | 0 | 0 | 0 | 0 | 783.75 | 281.82 | 59.04 | 580.83 | 481.78 |

The results show that samples 2, 5 and 6 have the best wicking efficacy (i.e., combination of distance traveled by the dye and weight gained). TABLE 2 also shows that surface treatment improves the wicking efficacy. At the scale of measurement used, Sample 1 showed no improvement over the control samples in terms of distance traveled but a small improvement in weight gain over control 3, and larger gains over controls 1 and 2. This demonstrates that Sample 1 has achieved some wicking efficacy in terms of weight increase.

There have been described and illustrated herein several embodiments of a conduit with wicking properties. While particular embodiments have been described, it is not intended that the invention be limited thereto, as it is intended that the disclosure be as broad in scope as the art will allow and that the specification be read likewise. Thus, while particular types of conduits and particular types of wicking elements have been disclosed, it will be appreciated that any suitable combination of conduits and wicking elements may be used to provide a conduit with wicking properties. In addition, while particular types of materials and shapes for the elongate ribs and/or projections, grooves and filaments have been disclosed, it will be understood that other types can be used. It will therefore be appreciated by those skilled in the art that yet other modifications could be made to the provided disclosure without deviating from its spirit and scope as claimed.

What is claimed is:

1. A medical circuit component for use with humidified gases, the medical circuit component comprising:

a body comprising a wall having an inner surface that defines a space within which the humidified gases flow and/or are contained, the wall being formed from a breathable material such that the wall is permeable to water vapor but substantially impermeable to liquid water and bulk flow of gases inside the medical circuit component; and a moisture transport means and/or element at least partially coupled to and/or at least partially integrated into at least a part of the wall, the moisture transport means and/or element being configured to receive moisture from vapors and/or liquid inside the space and transport at least some of the moisture away from where it is received, the moisture transport means and/or element comprising one or more elongate ribs and/or projections, and the one or more elongate ribs and/or projections comprising at least one cut-out or groove.

2. The medical circuit component of claim 1, wherein the moisture transport means and/or element forms at least a portion of the inner surface of the at least a part of the wall.

3. The medical circuit component of claim 1, wherein the at least one cut-out or groove comprises one or more of: a slit, at least one narrow-mouthed V-shaped notch, a rectangular notch, and a flat top surface.

4. The medical circuit component of claim 1, comprising at least one reinforcing rib and/or projection providing structural support to the body of the medical circuit component.

5. The medical circuit component of claim 1, wherein the moisture transport means and/or element comprises one or more filaments.

6. The medical circuit component of claim 5, wherein the medical circuit component is a corrugated tube and at least a first portion of the one or more filaments is secured in place by a portion of the wall and at least a second portion of the one or more filaments is disposed within the space within which the humidified gases flow and/or are contained.

7. The medical circuit component of claim 1, further comprising a heating means configured to heat the humidified gases and/or the wall.

8. The medical circuit component of claim 1, wherein the medical circuit component comprises one of or is a part of: an expiratory and/or an inspiratory tube in a dual limb circuit; a tube in a single limb circuit; a tube in a breathing circuit; a tube in an insufflation circuit; a tube in a surgical circuit; and a tube in an anesthesia circuit.

9. The medical circuit component of claim 1, comprising three elongate ribs and/or projections equally spaced apart about a circumference of the inner surface of the wall.

10. The medical circuit component of claim 1, wherein the moisture transport means and/or element is completely coupled to, fully integrated with, or formed integrally with the at least a part of the wall.

11. The medical circuit component of claim 1, wherein the medical circuit component has a major axis and the one or more elongate ribs and/or projections extend along at least a part of a length of the medical circuit component along the major axis.

12. The medical circuit component of claim 11, wherein the at least one cut-out or groove extends along at least a portion of the length of the one or more elongate ribs and/or projections.

13. The medical circuit component of claim 12, wherein the one or more elongate ribs and/or projections comprise a base portion adjacent the wall and the at least one cut-out or groove is formed at or near the wall.

14. The medical circuit component of claim 1, wherein at least a portion of the moisture transport means and/or element is formed from the breathable material.

* * * * *